(12) United States Patent
Behrends et al.

(10) Patent No.: US 9,403,184 B2
(45) Date of Patent: Aug. 2, 2016

(54) METHOD FOR THE AUTOMATED PRODUCTION CONSISTING OF A MOLECULAR LAYER OF AMPHIPHILIC MOLECULES AND A DEVICE FOR PRODUCING SAID MOLECULAR LAYER

(75) Inventors: Jan Behrends, Stegen (DE); Gerhard Baaken, Feiburg (DE)

(73) Assignee: Albert-Ludwigs-Universität Freiburg, Freiburg (DE)

(*) Notice: Subject to any disclaimer, the term of this patent is extended or adjusted under 35 U.S.C. 154(b) by 319 days.

(21) Appl. No.: 13/979,129

(22) PCT Filed: Jan. 10, 2012

(86) PCT No.: PCT/EP2012/000081
§ 371 (c)(1),
(2), (4) Date: Oct. 22, 2013

(87) PCT Pub. No.: WO2012/095299
PCT Pub. Date: Jul. 19, 2012

(65) Prior Publication Data
US 2014/0044866 A1 Feb. 13, 2014

(30) Foreign Application Priority Data
Jan. 10, 2011 (DE) .......................... 10 2011 008 205

(51) Int. Cl.
*B05D 1/40* (2006.01)
*G01N 33/50* (2006.01)
(Continued)

(52) U.S. Cl.
CPC ................ *B05D 1/40* (2013.01); *B81C 1/0038* (2013.01); *G01N 33/5076* (2013.01); *B05C 11/023* (2013.01); *B05C 11/08* (2013.01)

(58) Field of Classification Search
None
See application file for complete search history.

(56) References Cited

U.S. PATENT DOCUMENTS 2,844,363 A * 7/1958 Clark ................................. 416/3
4,093,757 A * 6/1978 Barraud .................. B05C 3/125
118/402
(Continued)

FOREIGN PATENT DOCUMENTS

CN        101704685 A    5/2010
DE    102010022929 A1   12/2011
WO   WO 2006/068619 A1   6/2006

OTHER PUBLICATIONS

Simonsen et al.; Structure of Spin-Coated Lipid Films and Domain Formation in Supported Membranes Formed by Hydration; Langmuir, 2004, 20, 9720-9728.*

(Continued)

*Primary Examiner* — Michael P Rodriguez
(74) *Attorney, Agent, or Firm* — Arnold & Porter LLP; Todd A. Lorenz

(57) ABSTRACT

The invention is related to a method and an apparatus for the automated fabrication of a molecular layer made from amphiphilic molecules, in particular lipids for a lipid bilayer membrane, in the apparatus, which has a support substrate for supporting the molecular layer, a rotation element, which can be rotated on top of the support substrate, and an actuator device, by means of which the rotation element can be automatically rotated, wherein the rotation element has an outer surface, which is formed hydrophobic at least in sections, the method having the following steps: placing a first solvent, which contains amphiphilic molecules, in a region above the support substrate; causing the automatic rotation of the rotation element above the support substrate; moving the first solvent between the support substrate and the rotation element by the interaction of the rotating rotation element with the first solvent, thus forming the molecular layer.

15 Claims, 17 Drawing Sheets

(51) Int. Cl.
*B81C 1/00* (2006.01)
*B05C 11/08* (2006.01)
*B05C 11/02* (2006.01)

(56) References Cited

U.S. PATENT DOCUMENTS

| | | | | |
|---|---|---|---|---|
| 4,199,265 | A | * | 4/1980 | Sanderson et al. ............ 366/274 |
| 5,106,561 | A | * | 4/1992 | Singh .................... B05D 1/206 |
| | | | | 264/165 |
| 2009/0120874 | A1 | * | 5/2009 | Jensen .................. B01D 69/02 |
| | | | | 210/638 |
| 2009/0167288 | A1 | * | 7/2009 | Reid ................ G01N 33/48721 |
| | | | | 324/72 |
| 2011/0084026 | A1 | * | 4/2011 | Freger ................... B01D 69/10 |
| | | | | 210/653 |

OTHER PUBLICATIONS

Speijer et al.; Critical Micelle Concentrations and Stirring are Rate-Limiting in the Loss of Lipid Mass during Membrane Degradation by Phospholipase A2; Biophysical Journal, vol. 70, May 1996, 2239-2247.*

Willems et al.; Adsorption and Conversion of Prothrombin on a Rotating Disc; Blood, vol. 82, No. 2 Jul. 15, 1993, 497-504.*

Ishimori, et al., "Development of eco-sensor based on bilayer lipid membrane for the continuous moniotring of environmental polutants," SPIE, PO Box 10 Bellingham WA 98227-0010 USA, Bd. 4199, Nr. 43, 2001, pp. 86-93.

Speijer, et al., "Critical Micelle Concentrations and Stirring Are Rate-Limiting in the Loss of Lipid Mass during Membrane Degradation by Phospholipase A2," Biophysical Journal, Bd. 70, Nr. 5, May 1, 1996, pp. 2239-2247.

Baaken, et al., "Planar microelectrode-cavity array for high-resolution and parallel electrical recording of membrane ionic currents," The Royal Society of Chemistry: Lab Chip, vol. 8, 2008, pp. 938-944.

Baaken, et al., "Towards a polymeric patch-on-a-chip design," European Cells and Materials, vol. 10, Suppl. 5, 2005, p. CS4.

Baaken, et al., "Towards a Polymeric Patch-on-a-Chip Design," Tissue Engineering, Abstract No. P 01, Session 2a: Nanofluidics and Interfaces, vol. 13, No. 4, 2007, p. 889.

\* cited by examiner

METHOD FOR THE AUTOMATED PRODUCTION CONSISTING OF A MOLECULAR LAYER OF AMPHIPHILIC MOLECULES AND A DEVICE FOR PRODUCING SAID MOLECULAR LAYER

The invention relates to a method for the automated fabrication of a molecular layer made from amphiphilic molecules, in particular a lipid bilayer, and an apparatus for the fabrication of said molecular layer.

Molecular layers made from amphiphilic molecules, in particular lipid bilayers (double lipid layers), are applied, for example, in the field of cell electrophysiology as well as for particular methods related to single molecule analysis, which are based on nano pores (molecular coulter counter). For realizing said applications, the voltage clamp technique ("voltage clamp") is employed, in particular, for achieving the precise measurement of the flow of charged particles (ions). The measurement of the ion flow is carried out by way of placing a dielectric (insulating) separation layer (membrane) between two compartments containing electrolyte solution, the separation layer containing at least one ion-permeable pore, or respectively, an ion channel. Said membrane can be a lipid bilayer, which is a typical basic element of natural biologic (cell-) membranes and which therefore can be used as an artificial model of a natural cell membrane. The voltage clamp technique requires that two compartments are electrically contacted, which are the regions on both sides of the membrane. For this purpose, the membrane is, usually, being fabricated above the aperture of a surface of a support substrate, wherein the aperture forms the upper edge of a micro cavity or a micro hole in the support substrate. In case of the lipid bilayer being placed above the surface, the corresponding molecular layer spans the aperture in a self-supporting way by means of its characteristic surface tension. Said arrangements are also referred to as "black lipid membranes" (BLM), because the apertures appear to be black under the optical microscope. Such methods and setups for the voltage clamp technique are described, for example, in Baaken et al. ("Planar microelectrode-cavity array for high-resolution and parallel electrical recording of membrane ionic currents", Lab Chip, 2008, 8, 938-944), also in Baaken, Prucker, Behrends, Ruhe 2005, European Cells and Materials 5, Suppl. 5, p. CS4; Baaken, Prucker, Sondermann, Behrends, Ruhe 2007, Tissue Engineering 18, 889, or also in US 2009/0167288 A1. Furthermore, it is also of interest to fabricate molecular layers on top of aperture-free substrates, in particular for fabricating the so-called "substrate supported membranes" ("supported membranes"), which can be used for a great many of applications, as is known.

For a long time researchers are occupied to fabricate such membranes on solid bodies as easy and reliably as possible. Known methods for fabricating such a molecular layer, in particular a lipid bilayer, on a surface include the method according to Langmuir/Blodgett/Langmuir-Schafer, the method of fusion of lipid vesicles, the painting method ("painting"). Some of said methods are summarized, for example, also by the document "Baaken et al." or US 2009/0167288 A1. The painting method provides to mechanically and manually "paint" lipids, which are solved in a solvent, e.g. decane, by means of a brush made from wire, across a surface, which may have an aperture, such that a lipid bilayer is being formed coplanar above the surface by way of the self-organization of the amphiphilic molecules. Said method has to be carried out by experienced experts, which means it is laborious and by trend disadvantageous considering that there is a requirement for suitable reproducibility of the so fabricated membranes. In particular, there is still a desire for a method for reliably fabricating such substrate supported molecular layers and, correspondingly, for thereby improving the sensor systems, which can be realized using the molecular layers, for example, for achieving a higher throughput of measurements.

It is the object of the present invention is to provide a method and an apparatus for the fabrication of a molecular layer from amphiphilic molecules, in particular a lipid bilayer, which, in particular, works as easy and reliably as possible.

According to the invention, the object is met by the method according to claim 1 and the apparatus according to claim 10. Preferred embodiments of the method or respectively, the apparatus used with the method, are subject matters of the sub claims 2 to 9.

The method according to the invention for the automated fabrication of a molecular layer made from amphiphilic molecules, in particular lipids for a lipid bilayer membrane, in an apparatus, which has a support substrate for supporting the molecular layer, a rotation element, which can be rotated on top of the support substrate, and an actuator device, by means of which the rotation element can be automatically rotated, wherein the rotation element has an outer surface, which is formed hydrophobic at least in sections, has the following steps:

placing a first solvent, which contains amphiphilic molecules, in a region above the support substrate;

causing the automatic rotation of the rotation element above the support substrate;

moving the first solvent between the support substrate and the rotation element by the interaction of the rotating rotation element with the first solvent, thus forming the molecular layer.

The method according to the invention has the advantage, in particular, that mechanically caused fabrication of the molecular layer is carried out by a non-manual, namely automatic, movement of the rotation element, whereby said fabrication is easy and reliable. The method uses, in particular, the apparatus according to the invention.

The apparatus according to the invention for the automated preparation of a molecular layer made from amphiphilic molecules on top of a support substrate has:

a support substrate for supporting the molecular layer;

a rotation element, which is arranged rotatable above the support substrate, and an actuator device, which automatically rotates the rotation element, wherein the rotation element has an outer surface, which is formed hydrophobic at least in sections, such that a solvent, which contains amphiphilic molecules, is moved on top of the support substrate during a rotation by the rotation element, thereby spreading the molecular layer.

Preferred embodiments of the apparatus according to the invention can be taken from the description of the method according to the invention, and vice versa.

The support substrate is, preferably, at least in sections or substantially completely formed planar. The support substrate can have one or more micro structures, i.e. spatial protrusions and/or recesses having small dimensions, which can amount, for example, to a few nanometers, several few micrometers, several few ten of micrometers or several few hundred micrometers. Such micro structures can be fabricated, for example, using known optic-lithographic methods, which include depositing in layers the structures, which have been defined by means of optical masks, on top of a support substrate and by removing the same in part.

The support substrate, preferably, has an upper side, which is planar at least in sections or substantially completely. The upper side, preferably, has at least one aperture, preferably a number N of apertures, wherein, respectively preferably, N is chosen between 2 and 2000, larger than 2000, preferably between 2 and 400, between 4 and 100, between 4 and 50 or between 4 and 20. An aperture can be used for example, for fabricating a self-supporting lipid bilayer membrane (BLM), as described at the beginning. Accordingly, the self-supporting molecular layer will separate two compartments from each other, which allows providing measurement arrangements for the realization of the voltage clamp technique. This will be explained later with reference to FIG. 4. The use of multiple apertures offers the advantage that multiple of such sensor systems can be operated in parallel, which allows for a higher throughput.

An aperture is understood to be the open cross section, which results, for example, by an opening, for example a recess or a hole, in a—in particular planar—surface of the upper side of the support substrate. The shape of the aperture contour is, preferably, circular, ellipsoid, triangular, quadrangular, or polygonal shaped. The maximum, the minimum or the average diameter of a single aperture is, preferably, smaller than 1000 µm an is, preferably, chosen between 500 nm and 500 µm, between 2 µm and 250 µm, or between 5 µm and 150 µm. Using such preferred aperture sizes (micro apertures), a molecular layer can be fabricated above the aperture, which is, usually, not possible in the case of macroscopic apertures having diameters of multiple millimeters.

Such apertures can be fabricated, for example, by the selective removal of a light sensitive layer, e.g. photoresist, which is formed on the surface of the support, by way of optical lithography, which is described, for example, by "Baaken et al." or US 2009/0167288 A1. However, the aperture can also form the edge of a hole, which extends from the upper side to the back side of the support substrate. This can be achieved, for example, by chemical etching or by irradiation with laser beams or other high energetic rays.

The arrangement having the number of N apertures, preferably, corresponds to an array, preferably to a periodic lattice, which allows to describe the position of the apertures or holes, respectively, by one or a few lattice parameter(s). The arrangement following a periodic lattice has advantages for designing a parallel sensor system, which is thought to provide preferably multiple measurement positions of similar type. The apertures, however, can also be arranged in a nonperiodic or not completely periodic pattern.

Preferably, the arrangement of apertures is such that all apertures are positioned completely within an area, which is swept by the rotation element, said area being defined by the rotation of a single rotation element. This way, multiple self-supporting molecular layers of completely similar type can be fabricated by means of a single movement of a single rotation element, which is of great advantage for achieving reproducibility and reliability of the sensor system provided thereby. Preferably, the apertures are concentrically arranged around a centre point, namely, preferably, along at least one circular path around said centre point or along multiple circular paths concentrically positioned around said centre point. The centre point is preferably arranged such that it corresponds to the centre of the rotation axis of the rotation element. The arrangement along a circular path involves the effect that the speed of the rotation element in each position of an aperture along a circular path is the same. By means of the rotation element the first solvent, which contains the amphiphilic molecules for forming the layer, is moved, thereby forming the molecular layer. Said movement is carried out, consequently, with the same speed at each aperture, such that membranes of similar type can be produced. This is a benefit for the reproducibility of the results of a fabrication of a molecular layer or a potential sensor system. Such a circular path, preferably, has a radius corresponding to at least five or ten aperture diameters up to millimeters. This offers advantages, when the first solvent spreads radially outwards starting from the centre by way of the action of the rotation element and the centrifugal force caused by the solvent's inertia. By way of said influences the movement of the first solvent radially outwards from the area around the centre of rotation is "normalized". This way, the same fabrication process is applied to each aperture. For this reason it is also preferred that no aperture is provided at least within an inner circular path around the centre point (acentric arrangement of the aperture/apertures). Nevertheless, it is possible and preferred that one or more apertures are arranged within said inner circular path around the centre point, which apertures are arranged acentric, in particular.

The support substrate is, preferably, fabricated by glass or contains glass. However, it can also consist of a semiconductor material or at least containing the same, e.g. Si/SiO2. Other materials are also possible. The upper side of the support substrate preferably has a coating. The coating, preferably, is hydrophobic, but can also be less hydrophobic and can also by hydrophilic. The advantage of a hydrophobic upper side is that many kinds of lipid bilayers are formed particularly reliable on such surfaces.

In the context of the present invention, a "hydrophobic" boundary layer is understood to be, in particular with reference to the design of the rotation element, a layer, on which a drop of water has a contact angle of at least 70°, preferably between 80° and 130° or between 90° and 120°. Therefore, the present definition of the term "hydrophobic" is broader than commonly known in literature, where the term usually refers to contact angles larger than 90°. Such contact angles (interior angle of the drop of water) can be easily measured by means of commercial devices for the measurement of contact angles or by the evaluation pictures of the drop taken in cross section with an optical microscope (e.g. taken at room temperature and standard conditions).

The coating of the support substrate, which preferably forms the upper side of the same and which preferably is hydrophobic, preferably consists of a light sensitive layer, in particular a photoresist, or contains the same. Said photoresist, preferably, is SU8, whose cured layers are hydrophobic. SU-8 is a commercial photoresist of the company Microchem Corp., USA, and belongs to the group of negative-resists. Similar to the most resists, SU-8 consists of the three basic parts including base resin, solvent and a photosensitive component. These are particularly suitable for providing the support substrate of the apparatus according to the invention, because many lipid bilayers, in particular, can be formed on top of said resists in a particularly reliable way, and because said resins can be processed by photolithography, e.g. for fabricating micro structures, and because they are relatively chemically inert.

Furthermore, the coating of the support substrate can contain, preferably, polytetrafluorethylene (PTFE) or can consist of the same. The advantage is that such layers are particularly chemically inert, thereby being particularly suitable for applications in corrosive environments (e.g. physiological electrolytes—physiological saline solutions).

The support substrate, preferably, is an integral part of the apparatus according to the invention. This is advantageous, e.g., when the same apparatus, in particular after being cleaned, is to be used with different molecular layers.

The support substrate can, however, also be provided to be a separate module, which can be detached from the apparatus, such that a molecular layer is fabricated on the support substrate by means of the apparatus according to the invention, and subsequently, the support substrate having the molecular layer is arranged differently with respect to the apparatus, and is, in particular, removed from the apparatus. As an alternative, also the support substrate can be arranged firmly, e.g. firmly on top of a measurement station, and the apparatus according to the invention can also be arranged transportable, i.e. be arranged movable, in particular with respect to the support substrate and/or the measurement station. In case that, this way, the support substrate and the apparatus according to the invention (i.e. its rotation element and/or its actuator device) are arranged to be displaceable in relation to each other, the advantage is achieved that numerous molecular layers can be fabricated on multiple support substrates by means of a single apparatus. This offers advantages, in particular, for providing an automatic process and a high throughput for the fabrication and measurement of such molecular layers.

It is also possible and preferred that multiple support substrates are arranged within a single apparatus, which may be arranged coplanar, in particular.

Preferably, the apparatus has a retaining device, by means of which the support substrate is retained, preferably detachably retained, in particular by means of a clamping device.

Preferably, a support substrate has at least one micro cavity, or preferably an array of micro cavities, wherein one or each micro cavity opens upwards and ends in one of said apertures (micro apertures) in the upper side of the support substrate. A micro cavity is a well in the upper side, wherein the depth of the well can have the same dimension as one of said preferred aperture diameters or can be deeper. Preferably, each cross section of the well is the same compared with the cross section of the apertures, which opens the micro cavity upwards. The micro cavity can be cylinder-shaped or cuboid-shaped, in particular. It can also be (truncated) cone-shaped or can have any other shape with varying cross section. A micro cavity can serve as a compartment, in which an electrolyte is placed for the purpose of contacting the lower side of a molecular layer arranged on the aperture. An electrode can be arranged on the bottom of the micro cavity for electrically contacting the electrolyte within the compartment (corresponding to the arrangement in FIG. 4a-c). A counter electrode placed in the electrolyte within the first compartment above the separating membrane can be used to realize a measurement arrangement for the voltage clamp technique.

Furthermore, a support substrate can have on its upper side at least one socket section or multiple socket sections, which preferably keep the rotation element, which rotates on the upper side, in a distance, wherein the rotation element may contact the socket sections but does not contact the region of the upper side, in which the molecular layer is supposed to be formed. A socket section can project from the upper side of the support substrate, e.g. forming a cam. The height of said socket sections can be, for example, 100 nm to 1000 µm, or 500 nm to 500 µm, or 1 µm to 250 ppm, or 50 µm to 250 µm. This way, the quality and uniformity of the membrane being formed can be further improved, because possible roughness of the contacting surface of the rotation element cannot directly take effect on the membrane (reduced "scraping"). A socket section can have any shape. Preferably, it has a planar surface, which promotes the rotating contact. Said surface preferably includes PTFE. A socket section can also be configured to be a guiding element, which guides the rotation element during the rotating motion, and can e.g. be configured to be a circular ring-shaped projection on the upper side of the support substrate. This way, it can be more precisely guaranteed that only selected regions of the contacting side of the rotation element may rotate above a target area, which selected regions may have a particular configuration (e.g. a coating), such that the molecular layer is produced in a defined way within said target region. Moreover, also the contacting side of the rotation element can have at least one or multiple socket sections, which may fulfil said purposes, if necessary.

Preferably, the apparatus has at least one wall section, which is arranged on top of the support substrate and which in combination with the support substrate defines a compartment, which may receive a liquid volume of several micro liters or preferably up to one milliliter. Consequently, the apparatus can have a compartment section for the reception of such a liquid volume, in particular of a first solvent (electrolyte) or second solvent.

Preferably, the rotation element is configured bar-shaped. By means of such a material-saving shape an area can be over-swept, which preferably corresponds to $(L/2)^2*pi$, wherein $L/2$ is the radius of the circular area, which is over-swept by the rotation of the contacting side of the rotation element. The rotation element contacts the support substrate within said circular area, or respectively, the layer of solvent arranged in said area, thereby forming the molecular layer within said circular area. In case that the rotation of the rotation element does not reach at least 360°, which is also possible, then the area being over-swept by the rotation is smaller than said circular area and corresponds to one or two segments of a circle.

The rotation element can be configured such that the value L for the diameter of the circle to be over-swept is between 1 mm and 100 mm, preferably between 3 mm and 15 mm, or between 5 mm and 10 mm. The rotation element can have any shape, but at least has a contacting side, which can effectively move and distribute the first solvent on top of an appropriately shaped support substrate. The rotation element, preferably, is bar-shaped or cuboid-shaped, has the length L and, furthermore, preferably has an average or maximum diameter D, wherein preferably D is between 0.5 mm and 25 mm, or between 1 mm and 10 mm, or preferably between 2 mm and 5 mm.

Preferably, the rotation element is a planar element, i.e. its average height is less than, preferably more than twice less than its average (or maximum) width and/or average (or maximum) length. The rotation element can, furthermore, also be disc-shaped, star-shaped (for example, three, four, five, six, or more spike elements), wheel-shaped (axis member with tire element(s) and spoke elements) or can be formed different.

The rotation element preferably has a contact side arranged facing the support substrate (or can be arranged this way). The contact side is used to contact the support substrate and/or the layer of the first solvent containing the amphiphilic molecules placed on the support substrate. By means of this contact, the first solvent is moved above the support substrate, thereby forming this molecular layer. The contact side is formed preferably hydrophobic or has hydrophobic portions. Such a portion may comprise or consist of PTFE. The outer surface of the rotation element can be at least partially or completely formed from a hydrophobic material, in particular polytetrafluoroethylene (PTFE). In case of PTFE, good properties of the contact side regarding the gliding capability, the mechanical durability and the chemical resistance are achieved. The contact side preferably is formed planar or is formed planar at least in sections.

The rotation element may comprise a mass element, which increases the total mass of the rotation element in a defined manner. The mass element may comprise or consist of metal or ceramic. Since basically every component has a mass, the mass element can also perform other functions, and can promote in particular the coupling between the actuator device and the rotation element. The resultant weight of the rotation element can apply a predetermined pressure to the contact surface or contribute for the weight. Using the mass element and providing the predetermined pressure guarantees that the first solvent is displaced during the rotation of the rotation element in a defined manner. This pressure is a parameter appropriate for influencing the quality and uniformity of the molecular layers with regard to the apparatus of the invention and the method for the fabrication of the molecular layers. Preferably, the pressure is generated only by the weight of the rotation element or formed differently. This pressure can be, for example, between 0.1 $kN/m^2$ (kilo-Newton per square meter) and 200 $kN/m^2$, and is preferably between 1 $kN/m^2$ and 20 $kN/m^2$ or between 2 $kN/m^2$ to 15 $kN/m^2$ or 4 $kN/m^2$ and 10 $kN/m^2$, as such values are especially suitable for the fabrication of lipid bilayers. The pressure may also be higher in some cases, preferably from 20 $kN/^2$ and A 50 $kN/m^2$ or between A 50 $kN/m^2$ and 100 $kN/m^2$ if necessary.

The rotation element may have a shaft coupling portion by which the rotatable shaft of the actuator device is coupled to the rotation element to convert rotation of the shaft in a rotation of the rotation element. The shaft coupling portion may provide a force-fit and/or form-fit and/or material bond connection of the shaft to the rotation element such as a screw, snap-in connection, clamp connection, adhesive bonding or welding connection. Moreover, the shaft coupling portion can be used in addition to providing the torque to provide a force to the rotation element with a force component perpendicular to the rotation plane. The direction of this force can point from the top onto the support substrate or point away from the same. The force can thus be used to make the rotation element "heavier" or "lighter", and thus to reduce or increase the pressure with which the rotation element is pressing on the support substrate. The shaft coupling portion may further include a spring portion, for example a connection socket made from a thermoelastic plastic material or a metal spring. Thus, a displacement of the shaft in the direction of the support substrate will cause a lower pressure increase between rotation element and the support substrate, as in the case without a spring connection. In this manner the pressure can be better adjusted and pressure fluctuations are damped. The shaft coupling portion and the spring element preferably allow a tilting of the shaft relative to the normal to a planar portion of the support substrate. In this way the rotation element may rest on the planar support substrate in each angular position of rotation, even if the shaft or the support substrate is inclined.

The apparatus may preferably comprise a number $N1$ of rotation elements and preferably a number $N2$ of rotation devices, wherein $N1, N2>1$, for example $1<N1, N2<100$, preferably $N1, N2<9$ or 17 Thus, a higher throughput in the fabrication of molecular layers can be achieved. The molecular layer support apparatus may thus have more than one rotation element, and a plurality of apertures in the support substrate may be preferably greater than or equal to the number of rotation elements, so that the inventive method may include the steps of:—causing the automatic rotation a plurality of rotation elements above the support substrate,—moving the first solvent above the support substrate by the interaction of the rotating rotation elements with the first solvent, thereby forming a molecular layer on more than one aperture.

The actuator device may comprise an electric motor to cause the rotation of the rotation element. The electric motor can cause rotation, directly or via a transmission device. A shaft driven by the electric motor may be directly or indirectly coupled to the rotation element. The actuator device may be adapted for mechanical interaction with the rotation element to effect rotation thereof mechanically, wherein the actuator preferably comprises a rotatable shaft which is kinematically linked to the rotation element. The shaft is preferably arranged perpendicular to the support substrate and preferably coupled to the geometric center or the center of mass of the support substrate. It is also preferred to rotate the rotation element through a ring-like bearing, wherein the ring may be disposed substantially parallel to the rotation plane of the rotation element. A guide member of the rotation element may then be circulated in this bearing and carry the rotation element.

The actuator device may have a z-actuator, which can deflect the rotation element at least partially in the direction (defined as the z-direction) perpendicular to a planar portion of the support substrate, and further, thus can apply a force. Preferably, the z-actuator comprises one or more piezoelectric elements, or consists substantially of the same. Further, preferably the actuator device comprises a force sensor by means of which the pressure may be, in each case preferably, controlled, regulated (controlled by closed-loop) and/or documented by utilizing the known size of the contact surface of the contact side of the rotation element. The force sensor may be a piezo-resistive sensor element. The force sensor can be incorporated directly in the shaft or can be connected to the z-actuator. By use of a controlled or regulated pressure, variations of the invention can be better adapted to individual needs in the fabrication of molecular layers with the method and the apparatus according to the invention.

Preferably, it may also be provided that the actuator device is formed for the contactless interaction with the rotation element to effect its rotation without contact, wherein the actuator device is designed in particular for generating a movable magnetic field, through which the rotation element is rotated. For this purpose a rotatable permanent magnet may be provided in the actuator device, having a bar-shape or other shape. Especially in the case of non-contact interaction, the rotation element is then further adapted to have a magnetic field, so that the moving magnetic field of the actuator device induces the movement of the rotation element by the magnetic interaction with the magnetic field of the rotation element. Very surprisingly it was found by the inventors in experiment series that an effective apparatus and method for the preparation of the molecular layer according to the present invention can be achieved by using a commercially available magnetic stirring bar as the rotation element that presses on the support substrate only by its proper weight. Although this embodiment is preferred, it is also possible and preferred that the rotary element has further advantageous structural features, for example, does not have a standard stirring bar.

Preferably the rotation element has a channel device, by means of which a liquid can be passed (for example, pressed) through the rotation element or along the latter in the direction of the support substrate or can be sucked away from the latter. The channel device may be connected to a suction system, which is preferably part of the apparatus, and in particular part of the actuator device, and which can be used for dosing the liquid. The channel device may be embodied as an opening in the rotation element, which may be in particular in the geometric center or center of mass of the rotation element. The channel device can be used in particular for guiding the first solvent containing the amphiphilic molecules to the support substrate, in particular for leading it directly to the center of rotation, from which it propagates to the outside, between the support substrate and rotation element. This is done from the center of rotation in a particularly even and effective manner, because the centrifugal force causes a radially outward acceleration of the first solvent, if it is made to rotate. The channel device configured as an orifice can be in particular funnel-shaped in order to technically simplify the addition of a liquid, in particular of the first solvent.

Furthermore, the rotation element can comprise a sensor device or parts of a measurement sensor device. Specifically, a capacitance meter may be provided, by having an electrode be provided at the contact side of the rotation element, by means of which impedance measurements can be carried out in particular during the rotation. Considering the known dielectric in the gap, the gap width can be determined, i.e. the distance between the contact side of the rotation element and the support substrate; if the gap width is known, the dielectric can be determined, and in particular the formation of a molecular layer can be assessed. Further, such an electrode may be used to monitor, during rotation, the electrical resistance through the molecular layer to a counter electrode, which may be located on the other side of the membrane. The counter electrode may be, for example, arranged directly on the support substrate, which is covered with the molecular layer, or may be incorporated into it, for example, be arranged in an electrolyte-filled micro-cavity having the aperture, above which the molecular layer is formed. For example, high resistances in the range of hundreds of megaohms or gigaohm can be used as a measure of the electrical quality of the seal and thus the quality of the molecular layers formed, in particular of the lipid bilayers. Such a measurement sensor device can comprise at least one component for an optical measurement, for example optical fibers, mirrors or lenses, in order to, for example, optically detect the rotation speed or the gap width.

Preferably, the apparatus comprises an electrical control device which is designed for automatically controlling the actuator device, in particular for automatically controlling or regulating the starting, stopping and speed of rotation. Such a control device may comprise a microprocessor and memory (of the type ROM and/or RAM), and data interfaces, and input and output devices of a user interface. The control device may include one or more control loops for regulating a physical parameter which is observable and modifiable, for example the pressure or the speed of rotation. The controller can be implemented programmable, so that the automation of the fabrication of molecular layers can be further improved, for example, by automatically adjusting, preferably program controlled, the rotational speed, pressure, or an automatic addition of liquid, in particular the first solvent, in response to measured values of the apparatus's own sensor device or an external sensor device. Furthermore, other measurements of the membrane or procedures in the apparatus may be automatically initiated automatically after detection of the successful fabrication of the membrane.

The method preferably provides to use a rotational speed of the rotation element, which is preferably from 0.1 revolutions per second (r/s), and 5 U/s. It has been found that especially those relatively slow rotational speeds are useful for the fabrication of molecular layers. The speed of rotation can also be defined differently, e.g., preferably less than 3 U/s, 5 U/s, 10 r/s, 20 U/s, 30 r/s, 40 U/s, 50 rev/s. The control device preferably is adapted to automatically set one or more rotational speeds, i.e. without any user adjustment of the speed being required, or is adapted to adjust by program control a sequence of gradually or continuously changing speeds, for setting the optimum speed pattern as a function of time for the individual fabrication of a molecular layer in dependence on a given solvent. The user simply selects the desired speed and the desired speed pattern, which is then set automatically by the apparatus.

The method preferably comprises the step that a molecular layer of amphiphilic molecules of sufficient quality results above a surface, which is at least once swept by the rotation element, in particular when the rotation element has performed a revolution of at least one 180° or 360° (that is, a full turn). This setting, surprisingly, was sufficient to achieve a successful fabrication of a molecular layer, in one embodiment of the method and apparatus. Preferably, at least 2, 3, 4, 5, 6, 7, 8, 9 or 10 complete revolutions of the rotation element are provided, preferably between 1 and 30, between 1 and 20, between 1 and 10, between 1 and 5, or between 1 and 3 full turns. A molecular layer of amphiphilic molecules of sufficient quality is understood to be, in particular, a bimolecular layer (for example a lipid bilayer), wherein the molecules are arranged in a stack of two molecular layers, which is in particular formed by self-assembly of the molecules. A molecular layer of amphiphilic molecules of sufficient quality is also preferably a substantially defect-free layer of molecules or molecular layer, which show electrical resistances of the molecular layer of at least 100 megohms, and respectively preferably, of at least 500, 1000, 5000 10,000 megohms, which may be measured, for example, by means of the voltage clamp technique. These molecular layers have a high "seal resistance" (high electric resistance).

Preferably, the apparatus includes at least one sensor device, which in particular has a sensor for electrophysiological studies on the molecular layer, in particular lipid bilayer. The sensor device may provide an electrode, which is arranged nearside to the molecular layer on the support substrate, for example, inside a micro-cavity, as previously described, and may also have at least one other electrode on the other side of the molecular layer, which other electrode is arranged in the electrolyte above the molecular layer. This sensor device is preferably configured to perform the voltage clamp technique by means of which, at constant voltage, the smallest currents in the nanoampere region can be measured and lower, in particular in the picoampere region, for example using a voltage-clamp and patch-clamp amplifier. The sensor device can have an array of sensors, which may be arranged in the support substrate or on its surface.

The apparatus may include a transport device by means of the support substrate and the rotation element are movable relative to each other. Preferably, the rotation element is movable perpendicular to the support substrate and is, in particular, automatically removable from the support substrate or approachable to the same. It is possible that a second transport device is provided, by means of which the support substrate or a plurality of support substrates, can be moved, in particular parallel to the support substrate, in particular in the horizontal direction, or the rotation element or the first transport device can be moved in this direction. Then, for example, molecular layers can be fabricated at high throughput on many support substrates successively "in the assembly-line system".

The first solvent for dissolving the amphiphilic molecules and their concentration in the first solvent should be selected so that the molecules, especially the lipids, are completely solved. Suitable parameters are to be chosen depending on the circumstances. First, the release of the molecules, respectively lipid molecules, must be fully granted, i.e. the critical concentration for a micelle formation (Critical Micelle Concentration, CMC) should be high, on the other hand the solvent used for dissolving the lipids (LM) should very be hardly or impossibly be miscible with aqueous solutions. Most suitable first solvents include, by trend, nonpolar substances, such as long-chain alkanes, for example five to 40 carbons connected as a chain, each particularly preferably pentane, hexane, heptane, octane, nonane, further for example, also decane, dodecane, hexadecane, etc. Preferably, the first solvent comprises a mixture of two, three, four or more of said materials or consists thereof. Other suitable first solvents, especially for dissolving lipids, can be taken, for example, from "Baaken et al" or US 2009/0167288 A1.

For use as the second solvent, that is the electrolyte, which is placed beyond and above the molecular layer to be formed, salt solutions are preferred, in particular physiological saline solutions, which allow the electrophysiological measurement of the molecular layer, e.g. a lipid membrane, and, contained therein, charge transporting pores, e.g., channel proteins. Suitable second solvents, in particular for carrying out measurements using the voltage clamp technique, are shown in "Baaken et al" or US 2009/0167288 A1.

Suitable amphiphilic molecules for the production of molecular layers are especially lipids, in particular lipids suitable for the formation of membrane-like lipid bilayer, as they are cited, e.g., in "Baaken et al" or US 2009/0167288 A1.

In many fields including basic academic research or pharmacological drug screening, the provision of a stable, simple, fast and reliable generation of a lipid bilayer as an artificial cell model, is a critical factor for various applications. Regarding the pharmacological drug screening, a high experimental throughput, in particular, is extremely important for a general productive work. Users employed with basic research benefit from the simplification in experimental runs, from a reduced apparatus and systemic effort and from a high variability in experiments with statistically unlikely events related to the study of membrane proteins or model membrane itself. In summary: The present invention increases the efficiency in experiments with model membranes for users in all electrophysiological and biophysical disciplines by generally significantly reducing the time investment for their implementation.

Further preferred embodiments of the inventive method and the inventive apparatus will become apparent from the following description of embodiments in connection with the figures. The same reference numerals denote substantially identical components.

FIG. 4b shows a detail view of FIG. 4a.

Figure 1:
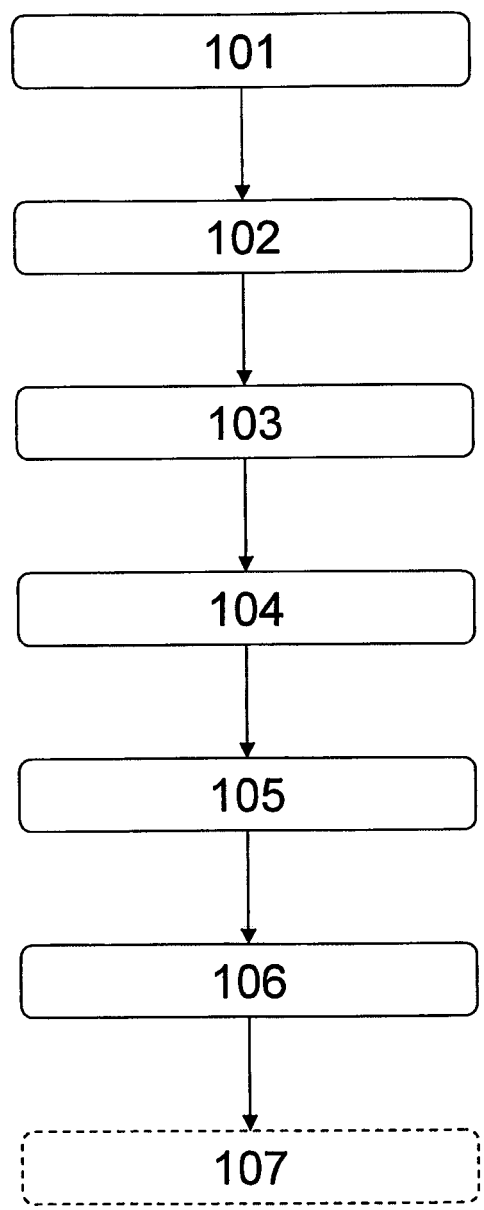
FIG. 1 shows schematically the course of an embodiment of the method according to the invention with reference to the embodiments of the apparatus according to the invention in FIGS. 2a to 4c.

FIG. 1 schematically shows the steps of the method to fabricate a lipid bilayer, for example by means of an apparatus according to one of the FIG. 2a, 3a, 3c or 4a, and then to measure the lipid bilayer.

Figure 2A:
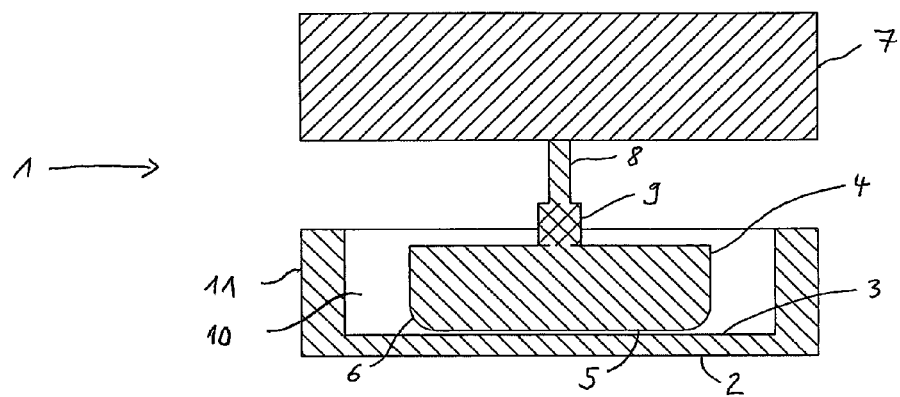
FIG. 2a shows a first embodiment of the apparatus according to the invention as a schematic cross-section.

The apparatus 1 of FIG. 2a comprises a support substrate 2 having a planar upper side 3. This upper side 3 is coated with SU8 photoresist, which is advantageous for the formation of double layers of amphiphilic molecules. Furthermore, this allows a relatively simple photolithographic microstructuring of the surface. In the upper side 3, micro cavities having a depth of 50 µm and having microapertures (50 µm diameter) are arranged as an array at intervals of 1 mm (not shown in FIG. 2a). The apparatus comprises a rotation element 4, which has a planar contact side 5 at its bottom. The rotation element is a bar-shaped element having rounded edges towards the bottom 6. The outer surface of the rotation element is coated with PTFE in the region of its side surfaces 6 and the contact face 5. This results in hydrophobic properties in this area, which is important for the manufacture of double layers of amphiphilic molecules.

The apparatus 1 of FIG. 2a also includes an actuator device 7, which comprises an electric motor that rotates the fixed shaft 8. The shaft 8 is coupled to the rotation element via a shaft coupling portion 9. This is formed as a spring element 9, which consists of a thermoelastic plastic material. In this way, the pressure of the rotation element 4 to the upper side 3 of the support substrate can be adjusted in a better way. The pressure at hand results from the deflection of the rotation element suspended at the spring element 9 and is approximately 5 $kN/m^2$. The apparatus 1 comprises a liquid-retaining chamber 10 placed on the support substrate 2, which chamber is formed from the support substrate and the wall sections 11.

Figure 2B:
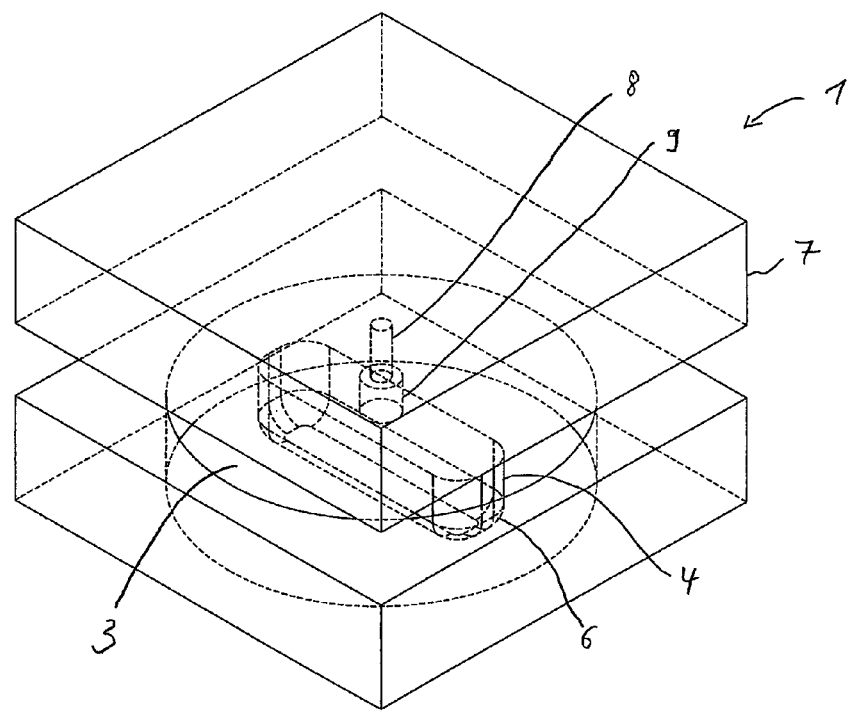
FIG. 2b shows the apparatus FIG. 2a in an isometric view.

FIG. 2b shows the spatial configuration of the apparatus of FIG. 2a in an isometric view. Dashed lines are actually hidden, and indicate the areas that actually would not be visible in this isometric view.

As shown in FIG. 1, the method for the production of the molecular layer, includes the steps of, first, to provide a solution of an amphiphilic molecule, here a lipid, e.g. Diphytanolphosphoditylcholin, solved in a suitable first solvent, such as decane, at a concentration at which a full solving is possible, here e.g. 1 mg/ml (step 101). A second solvent, the aqueous electrically conductive electrolyte containing dissolved salts is placed into the region of the chamber 10 (FIG. 2a) above the support substrate 2 (step 102). Then, a few microliters of the second solvent containing the lipid are dropped by means of a capillary body deposited above the upper side 3 and above the microcavities of the support substrate (step 103). Due to the poor solubility of the first and the second solvent, a mixing does not take place. The capillary can be moved manually or preferably automatically. The capillary is a glass capillary, a pipette tip or other channel element, by means of which the first solvent stored in the capillary may be dispensed through the application of pressure by. The capillary can be integrated as part of a channel device in a rotation element (see below FIG. 3c). Then, the actuator device 7 with the rotation element 4 is brought to a predetermined position, in which the rotation element 4 applies the predetermined pressure on the support substrate 2 (step 104), which position was previously determined. The first solvent is located in a gap between the contact side 5 of the rotation element 4 and the upper side 3 of the support substrate 2 (see FIG. 2*a*).

Now, the rotation element is automatically rotated at a predetermined speed, e.g. 2.5 to 3.5 r/s (step 105). The movement of the first solvent on the upper side 3 and above the microapertures and microcavities now surprisingly successfully favors the formation of double lipid layers on the microapertures, thereby forming BLM (step 106).

Reasons for the success of the method and the apparatus according to the invention are found to be the defined and uniform motion of the lipids by the hydrophobic mechanical rotary body, which automatically applies and spreads the first solvent more uniform and ideal. The fact that the lipid solution is spread by the rotational movement between two similarly hydrophobic surface (herein SU8 and PTFE) facilitates the continued success of the formation of the lipid bilayer. Compared with the manual painting method, the waiting time of typically a few seconds to form a bilayer is eliminated. In the present invention, the double layers form rather in the first second of rotation.

Figure 3A:
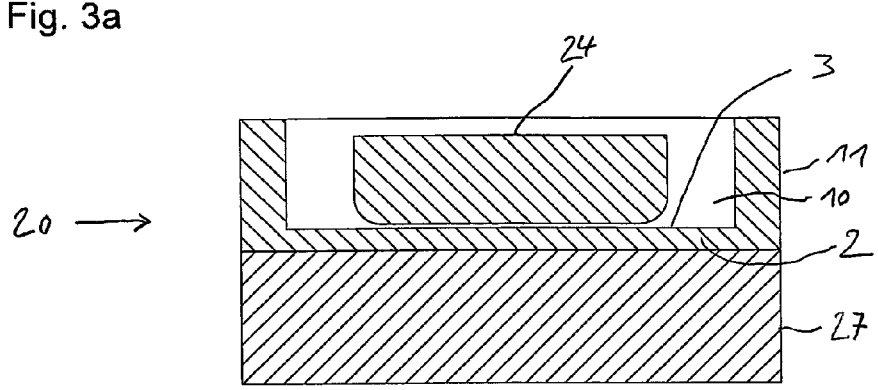
FIG. 3a shows a second embodiment of the apparatus according to the invention as a schematic cross-section.
Figure 3B:
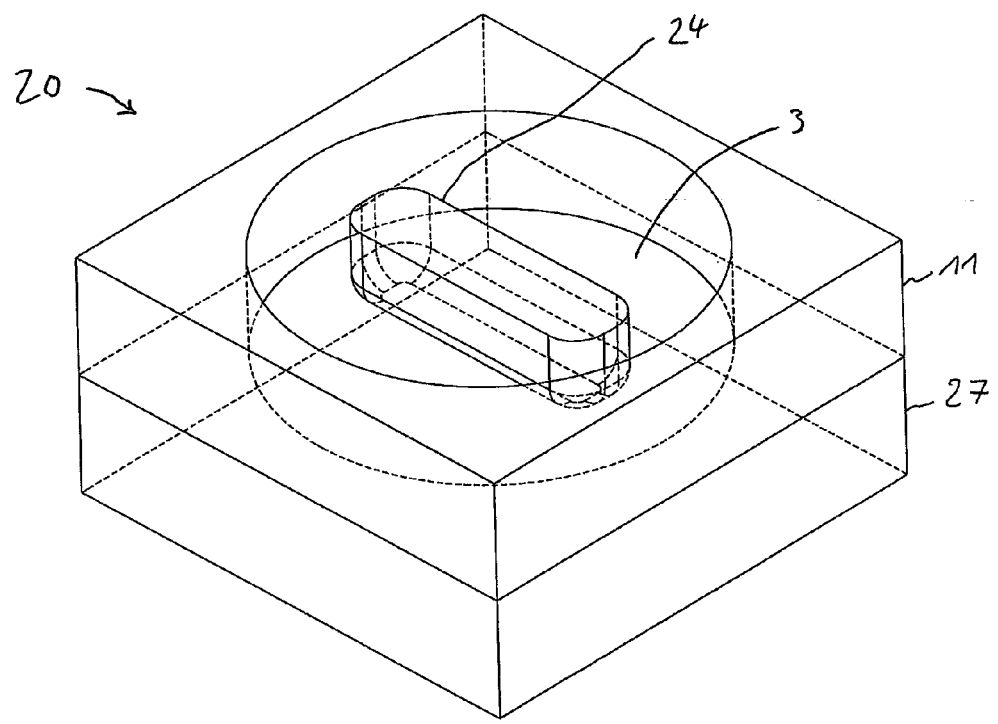
FIG. 3b shows the apparatus of FIG. 3a in an isometric view.

FIG. 3*a* shows an apparatus 20, in which the rotary body 24 replaces the rotary body 4 of FIG. 2*a*. Rotation element 24 comprises the same characteristics (shape, PTFE coating) such as rotation element 4, but has a means of contact-free coupling with the respective actuator device 27, instead of using the mechanical connection with the actuator device, as shown a shaft 8 and the shaft coupling portion 9 in FIG. 2*a*. For this purpose, a rotation element 24 has a core of a bar-shaped permanent magnet, whose magnetic field interacts with the rotating magnetic field formed by the actuator device 27 to rotate the rotation element 24. The actuator device 27 has, for this purpose, a direct-current electric motor, which rotates a bar-magnet disposed within the actuator device at the desired speed. This speed corresponds to the desired rotation for the rotational speed of the rotation element 24. Due to the contactless coupling of the rotation even more uniform rotational motion is possible, which further promotes the formation of lipid bilayers (BLM).

Figure 3C:
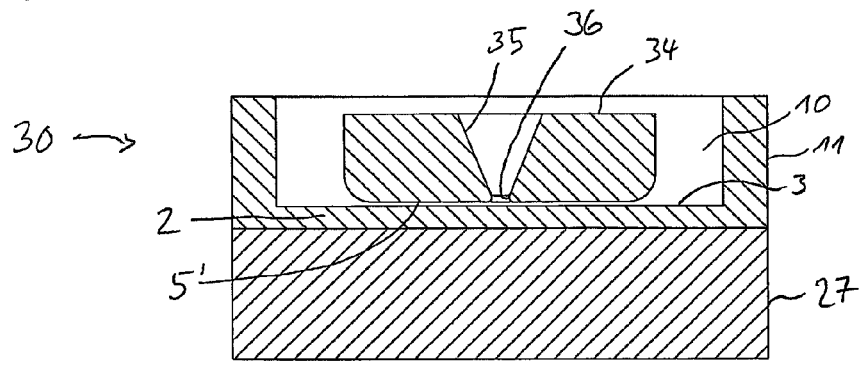
FIG. 3c shows a third embodiment of the apparatus according to the invention as a schematic cross-section.
Figure 3D:
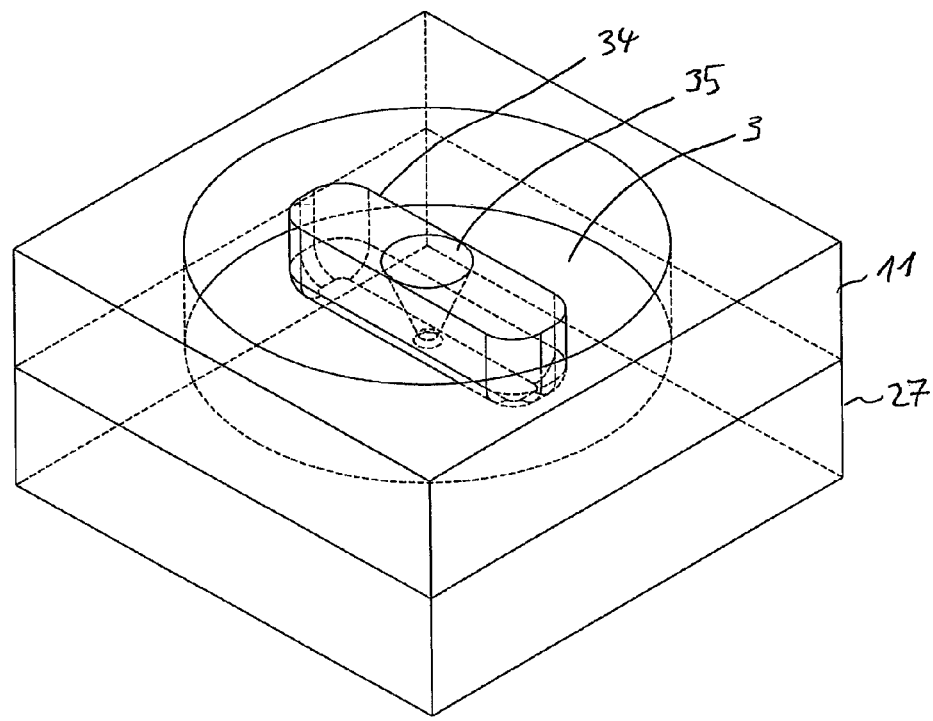
FIG. 3d shows the apparatus of FIG. 3c in an isometric view.

FIG. 3*c* shows an apparatus 30 similar to the apparatus 20 in FIG. 3*a* except for the differently configured rotation element 34. The rotation element 34 has a channel device, which, in this case, is formed as a funnel-shaped opening 35, by means of which the first solvent may be passed through the rotation element 34 to the upper side 3 of the support substrate 2. The channel device terminates in the geometric center of rotation of the rotation element 34 via an opening portion 36, which widens again directly at the contact side 5' of the rotation element 34. The first solvent being forced to flow through the channel 3 to the upper side of the support substrate will be radially spread from there to the outside by support of the rotation.

Figure 4A:
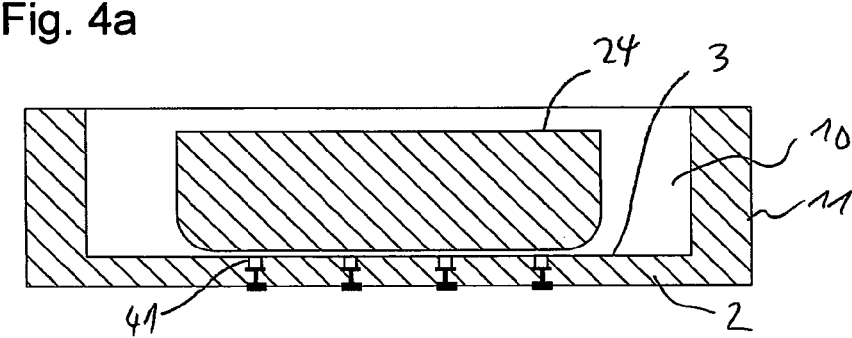
FIG. 4a shows a fourth embodiment of the apparatus according to the invention as a schematic cross-section.
Figure 4B:
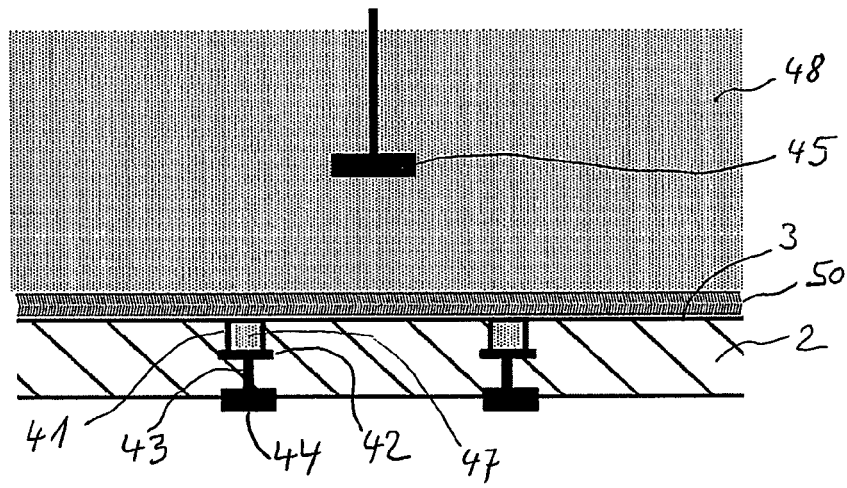
Figure 4C:
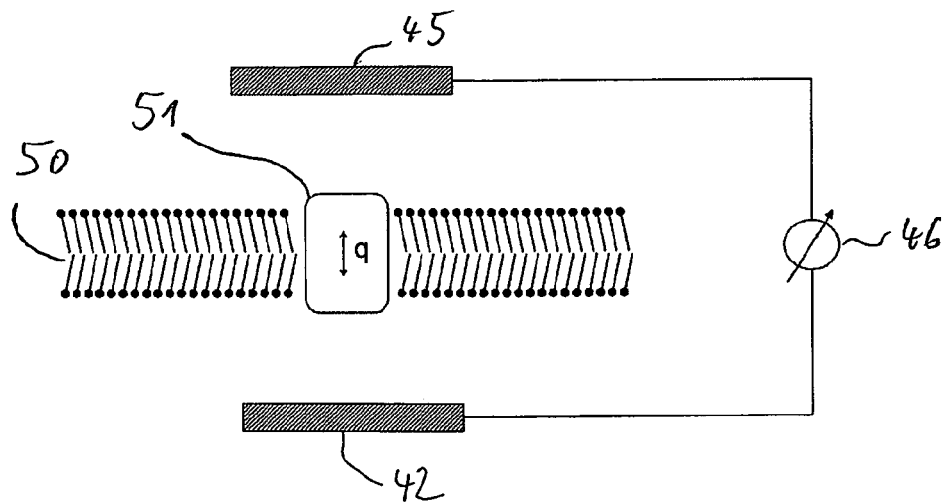
FIG. 4c shows schematically a measurement arrangement which is implemented using the inventive apparatus of FIGS. 4a and 4b.
Figure 5A:
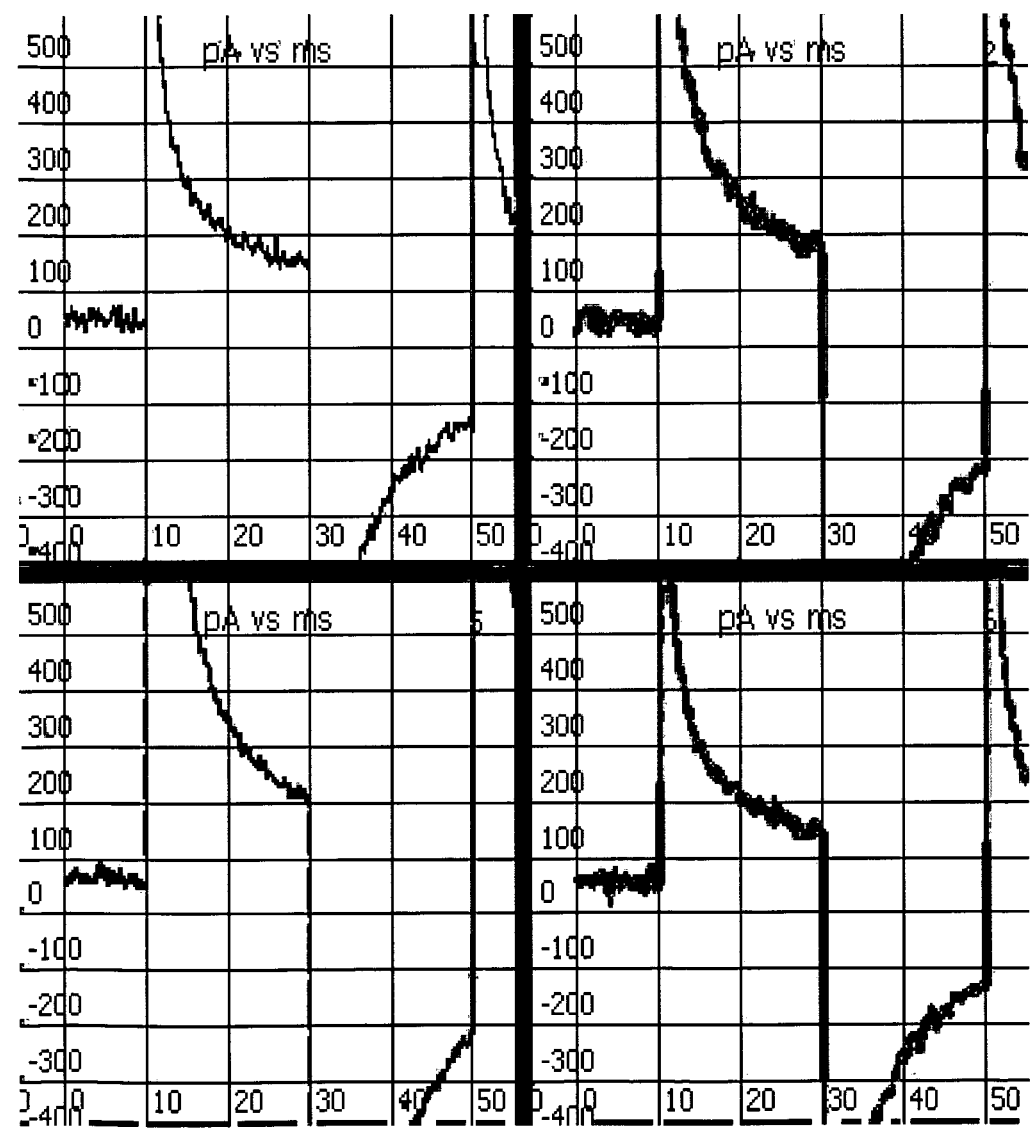
FIGS. 5a, 5b, 5c, 5d, 6a, 6b, 6c, 6d, 7a, 7b, 7c and 7d show measurement results on a lipid bilayer, which was prepared according to the invention and was measured by means of the measurement arrangement shown in FIGS. 4a to 4c.
Figure 5B:
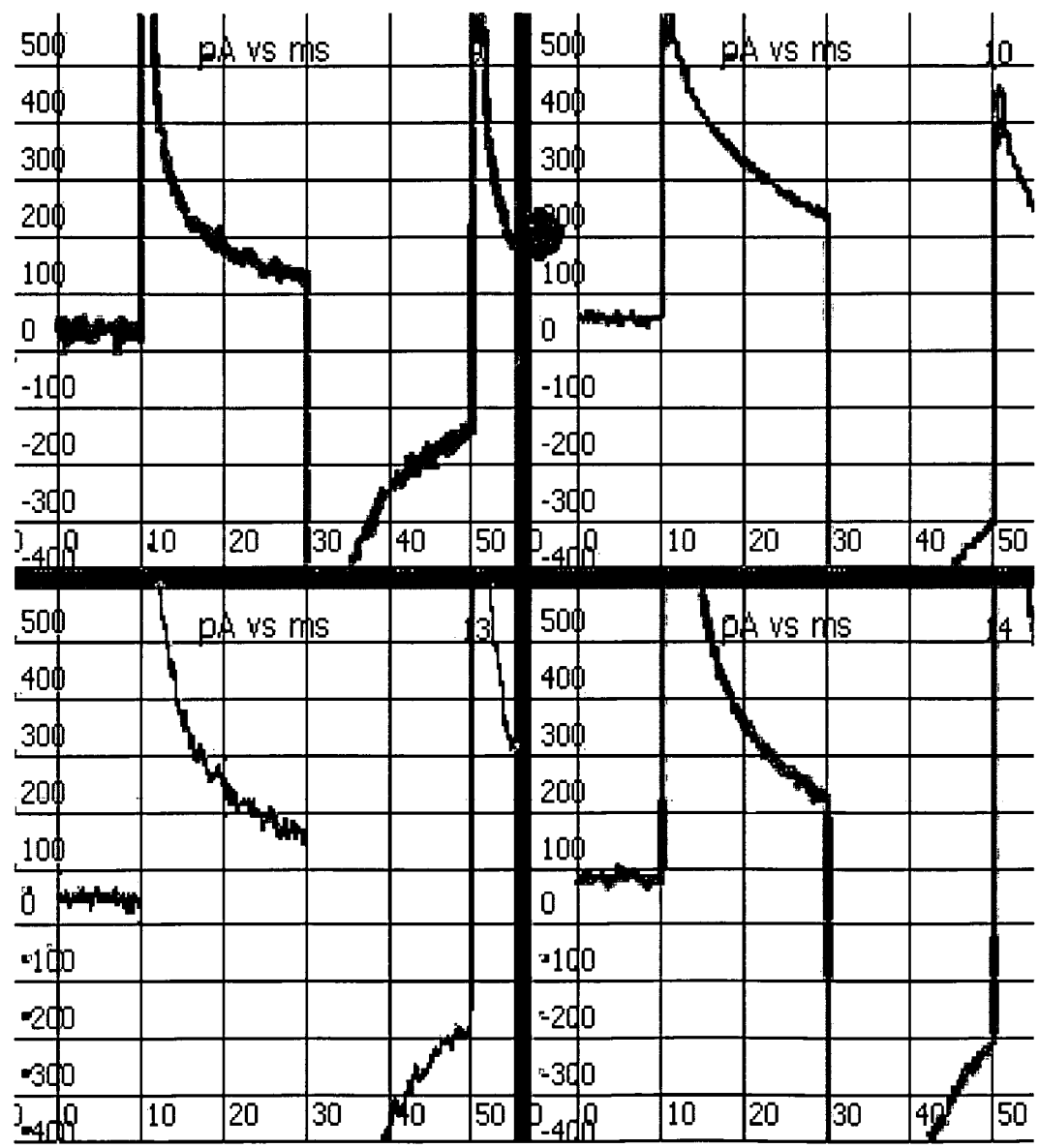
Figure 5C:
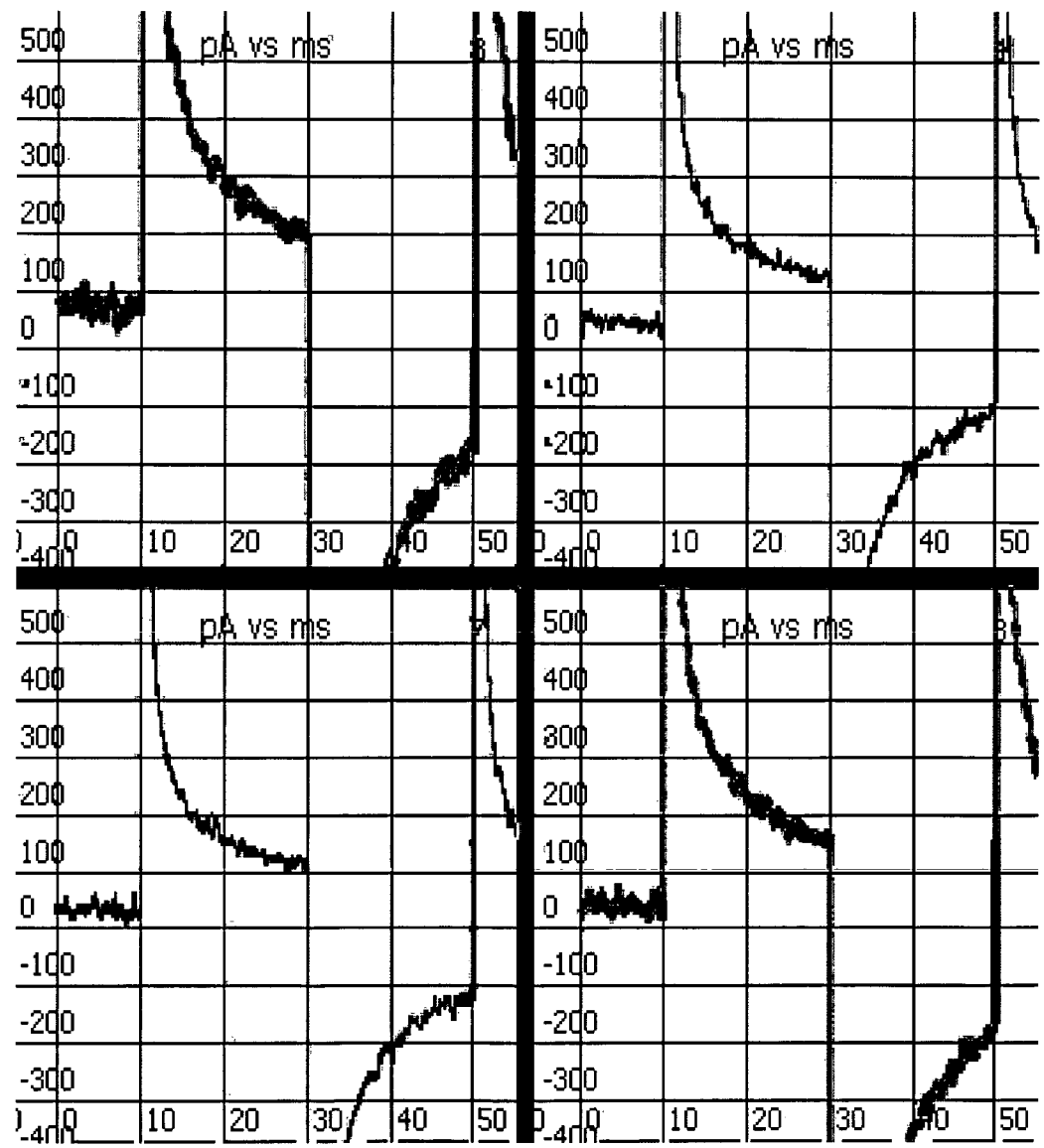
Figure 5D:
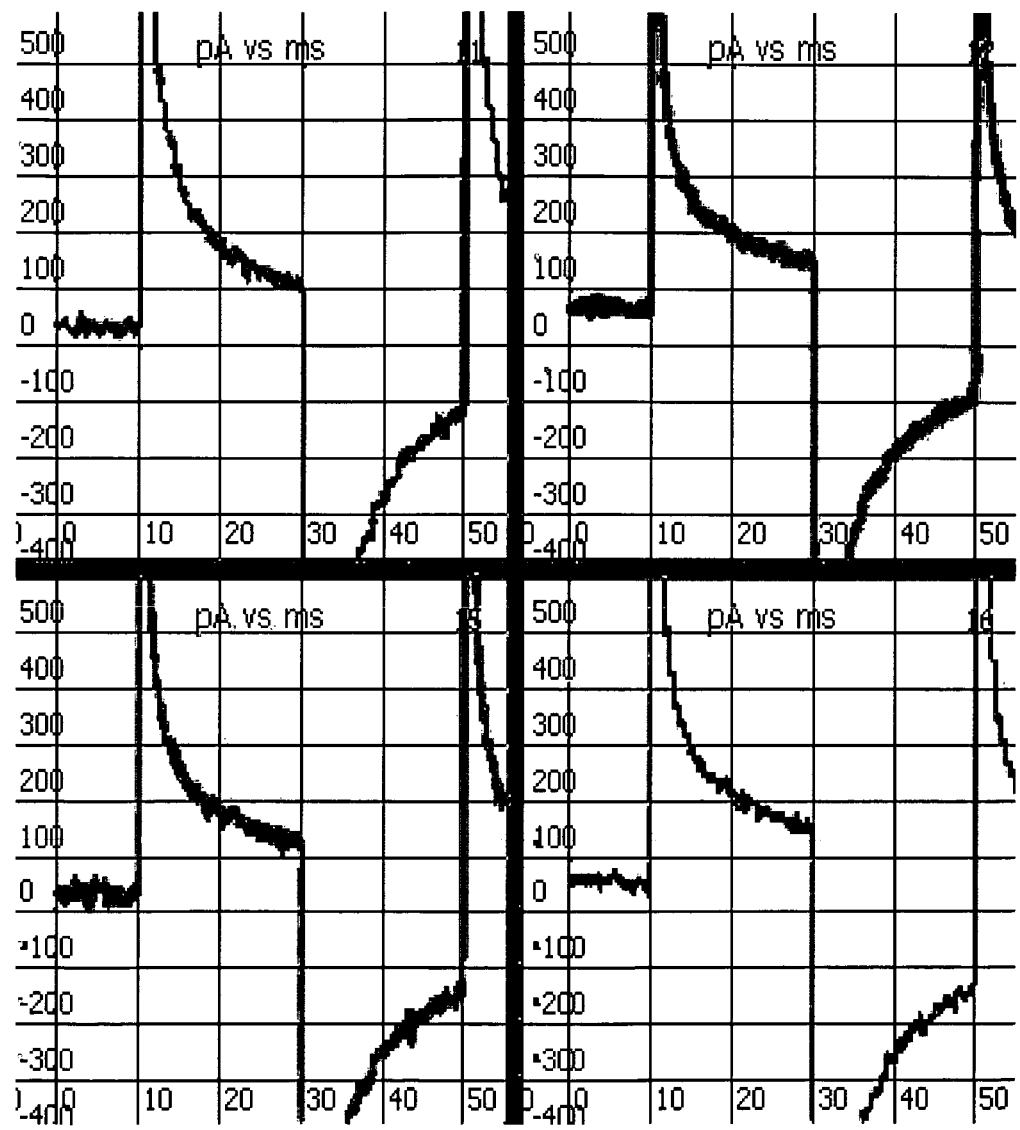
Figure 6A:
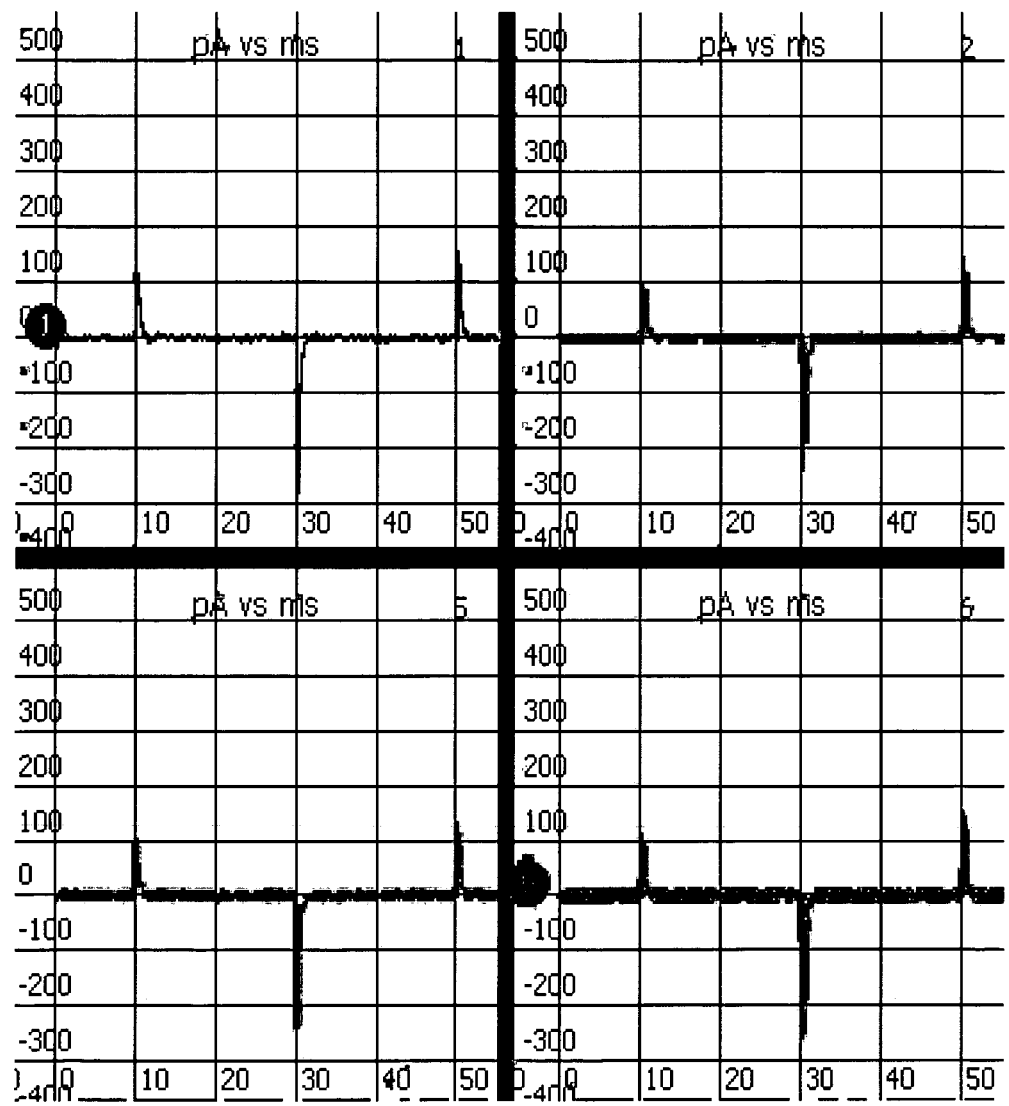
Figure 6B:
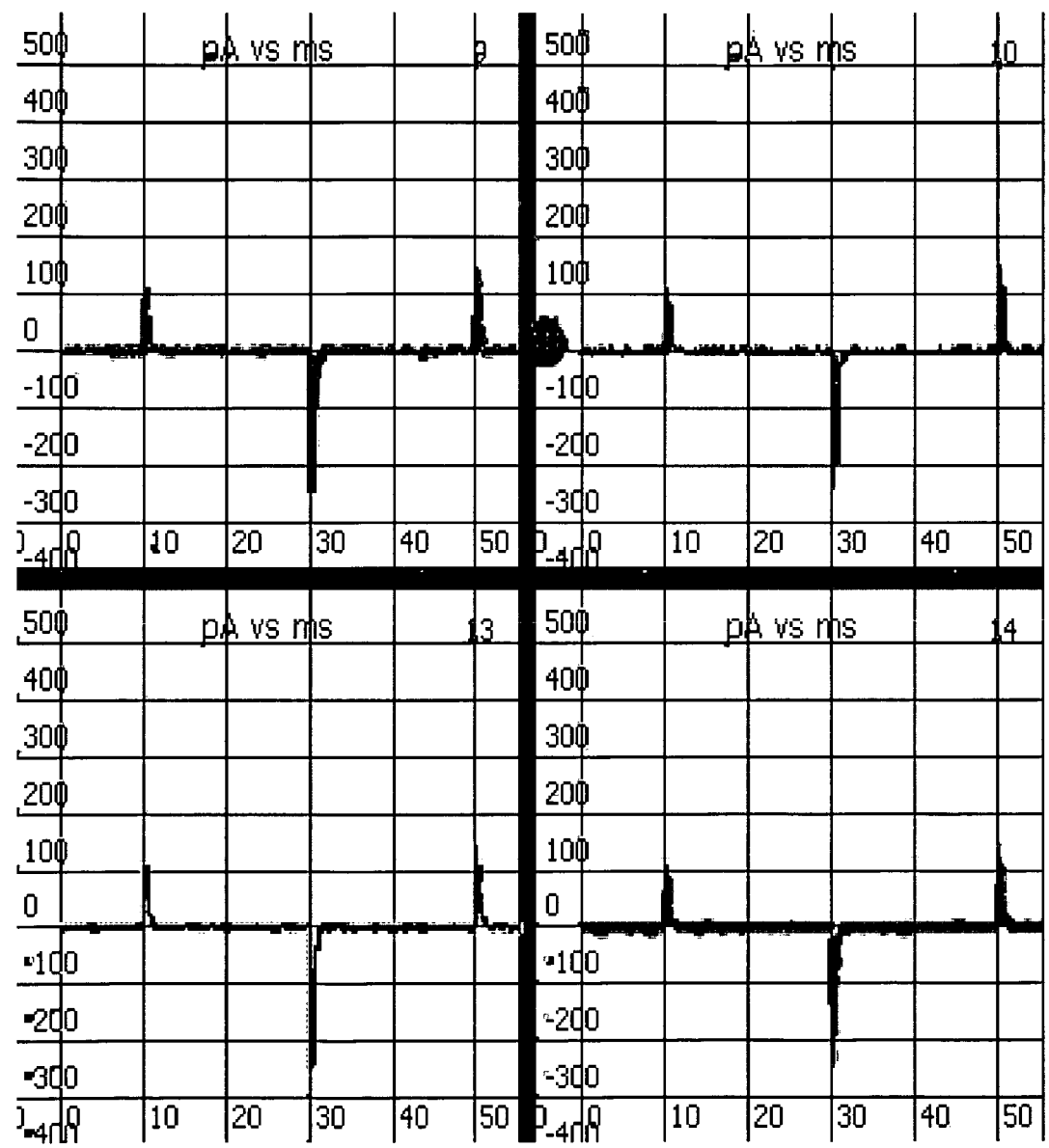
Figure 6C:
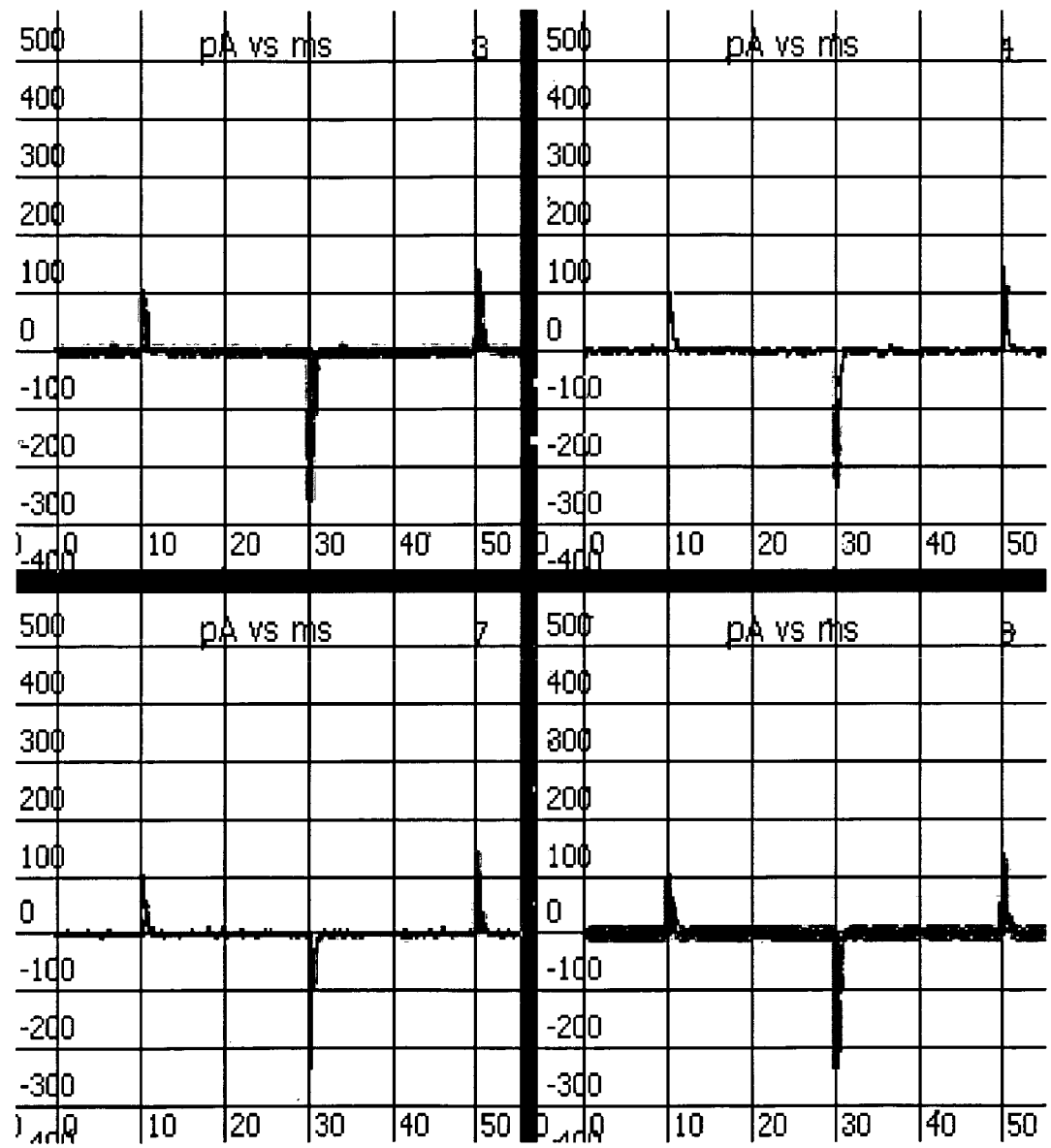
Figure 6D:
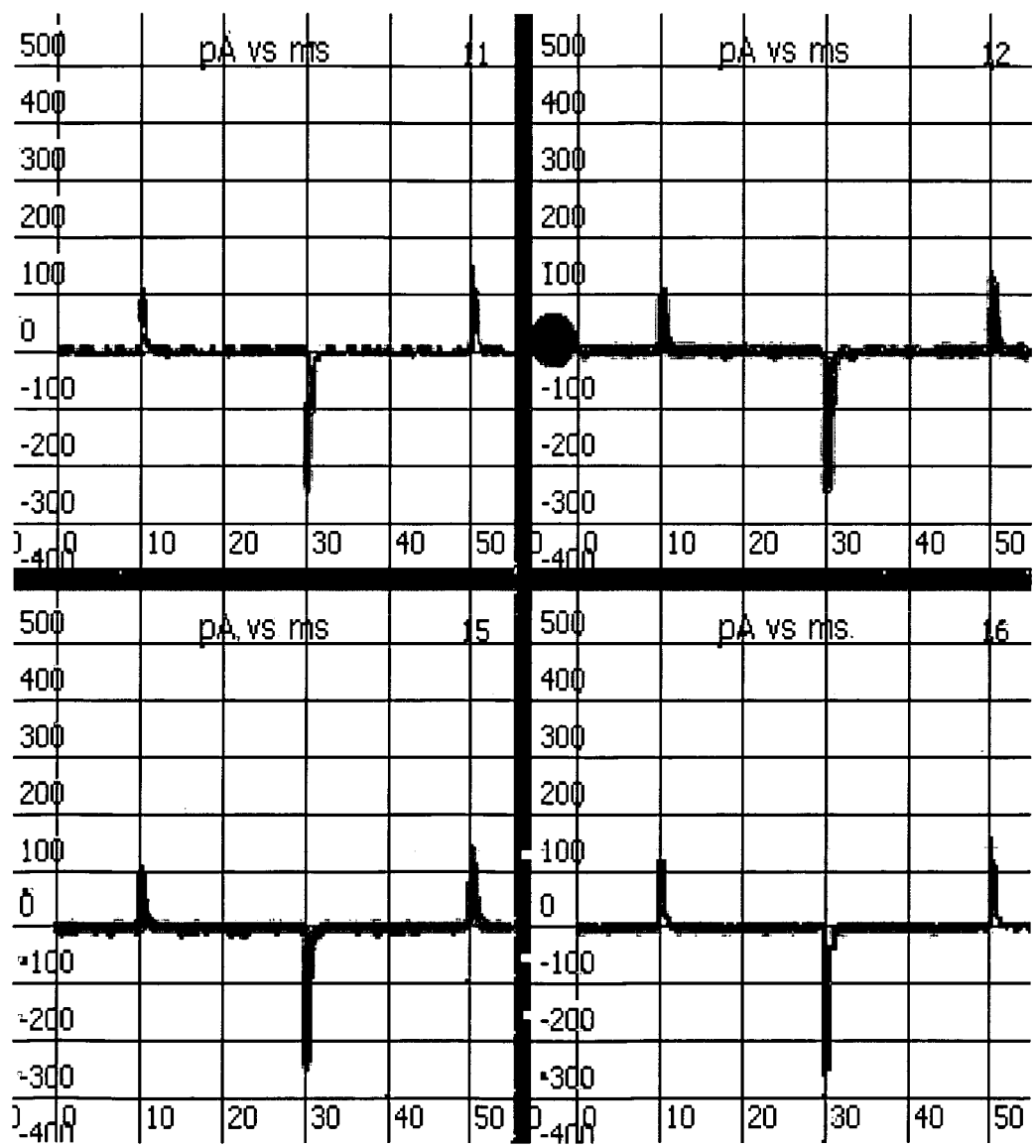
Figure 7A:
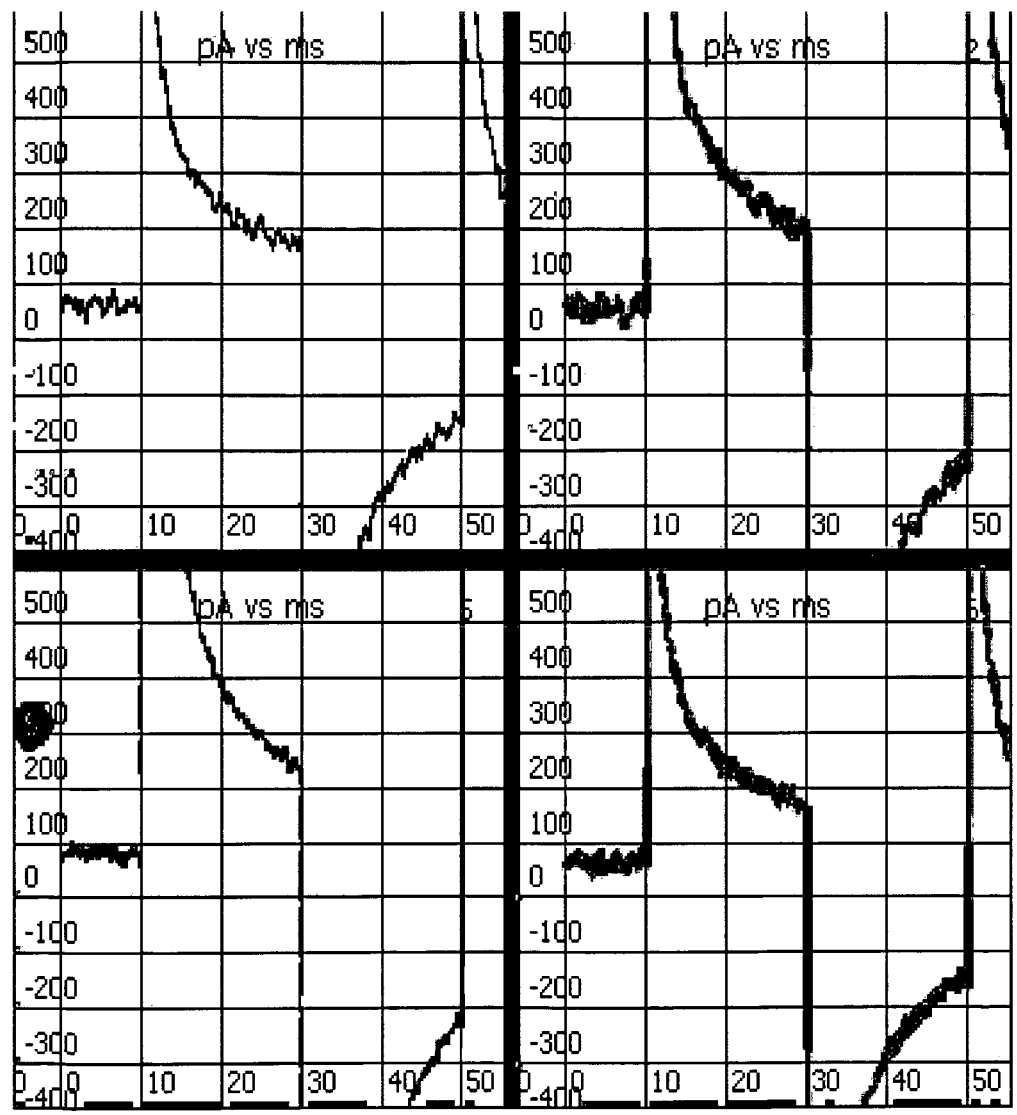
Figure 7B:
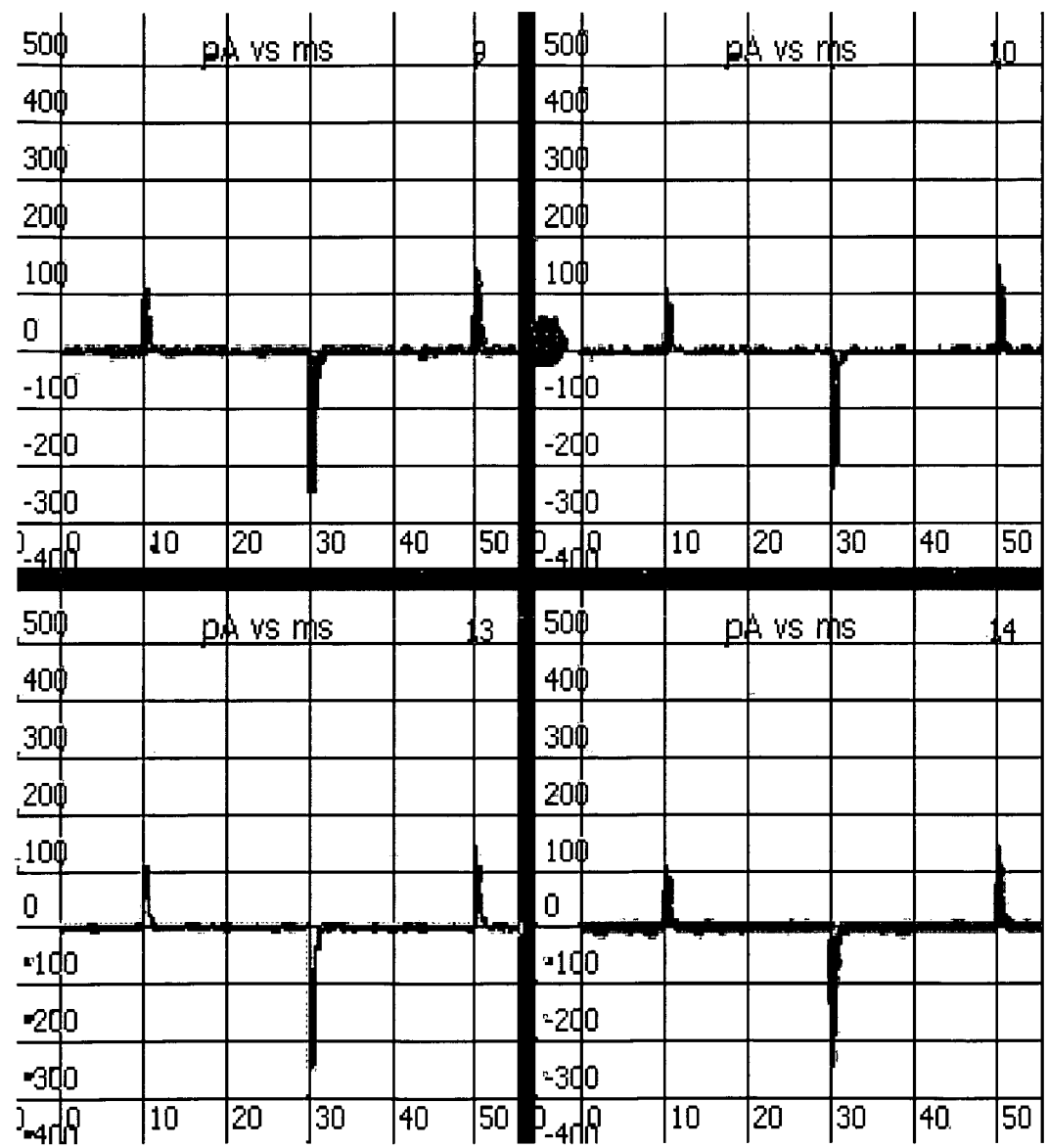
Figure 7C:
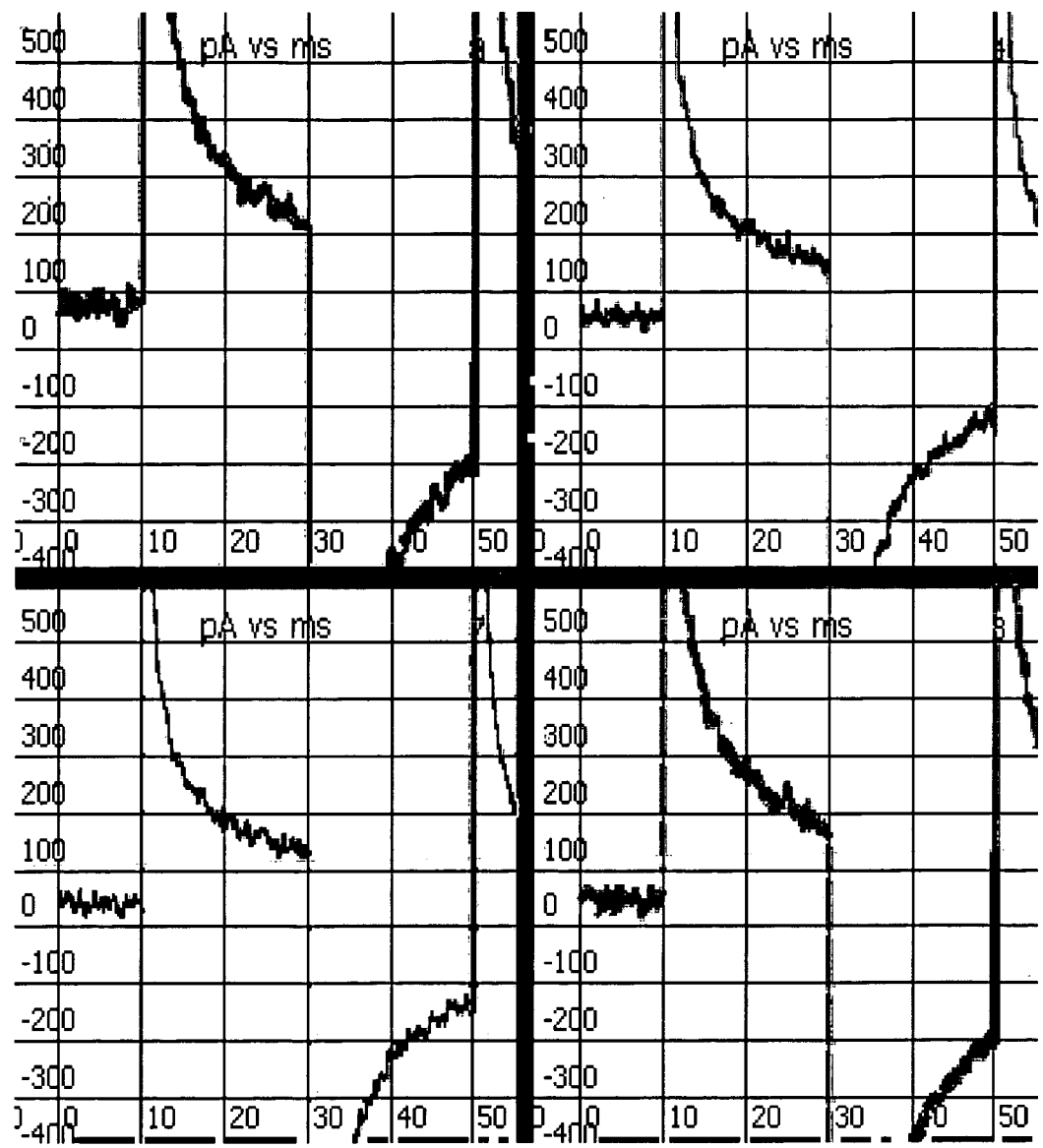
Figure 7D:
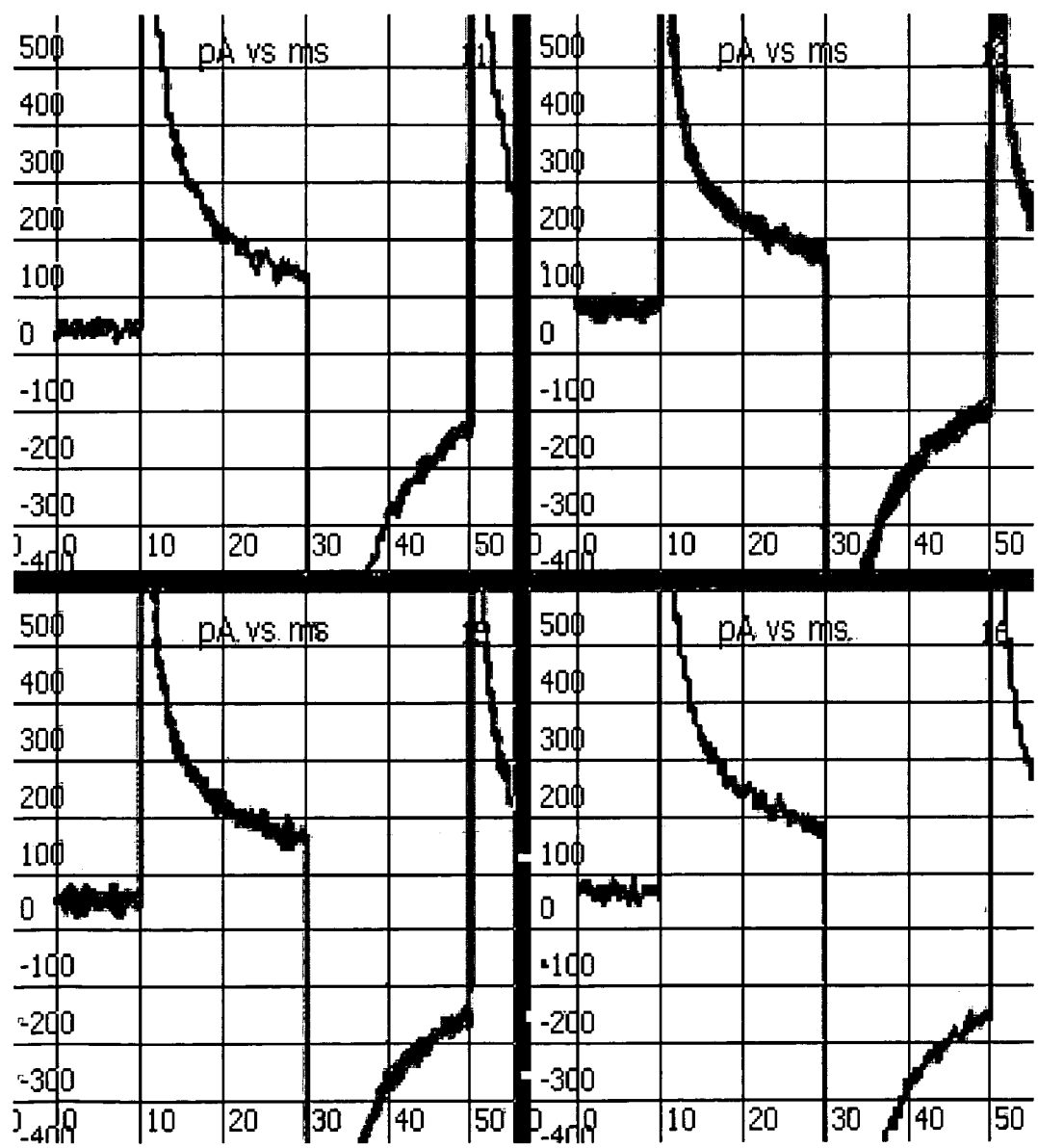

FIGS. 4*a* to 4*c* show how measurements can be performed on the lipid bilayer after forming the lipid bilayer on the upper side 3 of the support substrate 2, in particular to assess the quality of lipid bilayer, in an optional step 107. This applies to all apparatus shown in FIGS. 2*a*-3*d*. By means of the method, lipids have formed a lipid bilayer above the microcavities 41 ending into open microapertures. Each microcavity 41 is filled with an electrolyte 47 and the electrolyte 48 is located in the chamber 10. Each microcavity is provided downwards at the bottom with an internal redox electrode 42 (Ag/AgCl, for example). This is electrically connected via a supply line 43, which may be lithographically produced, to the outer contact 44, which may be used to connect a sensor device. A redox electrode 45 placed in the electrolyte 48 of the chamber 10 serves as a reference electrode for each of the individual electrodes, which are arraged in the micro-cavities. By using the voltage clamp technique, in which an electric potential across the membrane is maintained constant, for example by using a patch-clamp amplifier, the lowest current changes of a current of charges "q" can be detected through the membrane. These charges can be caused by the ion transport by leakage of the cell membrane or can be caused by pores, such as channel proteins 51 in the cell membrane.

FIGS. 5*a* to 7*d* show measurement results of measurements using a setup as shown in FIGS. 4*a*-4*c*. The simultaneous fabrication of lipid bilayers on a 16-micro electrode cavity array (MECA) is implemented by rotating the rotation element above these micro electrode cavities, or by a single sweeping of the rotation element above the microapertures of the micro electrode cavities. Three screenshots are shown of the control program for the 16-channel amplifier Tecella-Jet, having 16 windows each, in each which the current waveforms are recorded at the individual micro electrode cavity over time. Each of the 16 individual plots of FIG. 5*a*, 5*b*, 5*c*, 5*d*, as well 6*a*, 6*b*, 6*c*, 6*d*, and as 7*a*, 7*b*, 7*c* and 7*d* shows a current-time diagram (pA vs. ms) having a scaling of the ordinate of −300 to 500 pA and a scaling of the abszissa from 0 to 50 ms. FIGS. 5*a*, 5*b*, 5*c*, 5*d*, respectively, show the current responses before each actuation of the rotation element; clearly visible are the large current changes in the size range of nano amperes in response to a biphasic (positive/negative) voltage command. FIGS. 6*a*, 6*b*, 6*c*, 6*d* shows respectively, immediately after completion of the movement that the microcavities are all electrically sealed; visible are remaining only some capacitive artifacts in the range of a few hundred pico-ampere. The membrane resistance is very high (Gigaohm range), there is "no" charge transport through the membrane. FIGS. 7*a*, 7*b*, 7*c* and 7*d* show each that the cavities are opened again after electroporation using a voltage pulse of 990 mV amplitude and 100 ms duration. Such behavior is proving the existence of a bimolecular lipid layer, because only here sufficiently high field strengths for electroporation can be achieved. The membranes, which can be fabricated by the invention, including the achieved high membrane resistances, are ideal for applications, where minimal transmembrane currents are to be detected, for example, to study the activity of single charge-transporting transmembrane proteins.

The invention claimed is:

1. A method for the automated fabrication of a molecular layer made from amphiphilic molecules in an apparatus, which has a support substrate for supporting the molecular layer, a rotation element, which can be rotated on top of the support substrate, and an actuator device, by means of which the rotation element can be automatically rotated, wherein the rotation element has an outer surface, which is formed hydrophobic at least in sections, the method having the following steps:

placing a first solvent, which contains amphiphilic molecules, in a region above the support substrate;

causing the automatic rotation of the rotation element above the support substrate;

moving the first solvent between the support substrate and the rotation element by the interaction of the rotating rotation element with the first solvent, thus forming the molecular layer.

2. The method according to claim 1, wherein the support substrate is planar and has at least one upper side with at least one aperture, and wherein the method includes the step that the molecular layer forms such that it covers the at least one aperture.

3. The method according to claims 1 or 2, wherein the support substrate has at least one micro cavity, wherein one or each micro cavity opens upwards and ends in an aperture in the upper side of the support substrate, and wherein the method includes the step that the molecular layer forms such that it covers the at least one aperture or multiple apertures.

4. The method according to claim 2, wherein the apparatus has one or more than one rotation element, wherein the number of apertures in the support substrate is larger or equal to the number of rotation elements, and wherein the method includes the following steps:
  causing the automatic rotation of the one or more rotation elements above the support substrate;
  moving the first solvent above the support substrate by the interaction of the rotating rotation elements with the first solvent, thus forming a molecular layer on top of more than one aperture.

5. The method according to claim 1, wherein the actuator device interacts mechanically with the rotation element for the purpose of mechanically causing rotation of the same.

6. The method according to claim 1, wherein the actuator device is formed for a non-contact interaction with the rotation element for causing rotation of the same in a non-contact way.

7. The method according to claim 1, wherein the outer surface of the rotation element is formed at least in part or completely by a hydrophobic material.

8. The method according to claim 1, wherein the apparatus for supporting the molecular layer has an electrical control device, which is formed for the automatic control of the actuator device.

9. The method according to claim 1, wherein the apparatus has at least one sensor device, which has at least one sensor for the electrophysiological measurement of the molecular layer.

10. The method according to claim 1, wherein the molecular layer is a lipid bilayer membrane and the amphiphilic molecules comprise lipids.

11. The method of claim 2, wherein the upper side has an array of apertures.

12. The method of claim 3, wherein the support substrate has an array of micro cavities.

13. The method of claim 5, wherein the actuator device has a rotatable shaft, which is kinematically coupled to the rotation element.

14. The method of claim 6, wherein the actuator device generates a movable magnetic field, by means of which the rotation element is rotated.

15. The method of claim 7, wherein the hydrophobic material is polytetrafluorethylene (PTFE).

* * * * *